(12) United States Patent
Morales et al.

(10) Patent No.: US 12,268,720 B2
(45) Date of Patent: Apr. 8, 2025

(54) BACTERIOPHAGE FOR TREATMENT AND PREVENTION OF E. COLI AND B. FRAGILIS INFECTIONS

(71) Applicant: Armata Pharmaceuticals, Inc., Marina del Rey, CA (US)

(72) Inventors: Sandra P. Morales, Sydney (AU); Igor P. Bilinsky, San Diego, CA (US)

(73) Assignee: Armata Pharmaceuticals, Inc., Marina del Rey, CA (US)

( * ) Notice: Subject to any disclaimer, the term of this patent is extended or adjusted under 35 U.S.C. 154(b) by 846 days.

(21) Appl. No.: 16/968,132

(22) PCT Filed: Feb. 7, 2019

(86) PCT No.: PCT/US2019/017129
§ 371 (c)(1),
(2) Date: Aug. 6, 2020

(87) PCT Pub. No.: WO2019/157231
PCT Pub. Date: Aug. 15, 2019

(65) Prior Publication Data
US 2021/0369798 A1     Dec. 2, 2021

Related U.S. Application Data

(60) Provisional application No. 62/627,725, filed on Feb. 7, 2018.

(51) Int. Cl.
*A61K 35/768* (2015.01)
*A61K 45/06* (2006.01)
*C12N 7/00* (2006.01)

(52) U.S. Cl.
CPC ............ *A61K 35/768* (2013.01); *A61K 45/06* (2013.01); *C12N 7/00* (2013.01); *C12N 2795/10132* (2013.01); *C12N 2795/10332* (2013.01)

(58) Field of Classification Search
CPC .................... A61K 35/768; C12N 7/00; C12N 2795/10132; C12N 2795/10332
See application file for complete search history.

(56) References Cited

FOREIGN PATENT DOCUMENTS

| EP | 2893933 A1 | 7/2015 |
|---|---|---|
| JP | 2009532055 A | 9/2009 |
| JP | 2016509998 A | 4/2016 |
| JP | 2017507913 A | 3/2017 |
| WO | 2007113657 A1 | 10/2007 |
| WO | 2014130540 A1 | 8/2014 |
| WO | 2015104388 A1 | 7/2015 |

OTHER PUBLICATIONS

Bruttin A, Brüssow H. Human volunteers receiving *Escherichia coli* phage T4 orally: a safety test of phage therapy. Antimicrob Agents Chemother. Jul. 2005;49(7):2874-8. (Year: 2005).*
Buc E, Dubois D, Sauvanet P, Raisch J, Delmas J, Darfeuille-Michaud A, Pezet D, Bonnet R. High prevalence of mucosa-associated *E. coli* producing cyclomodulin and genotoxin in colon cancer. PLoS One. 2013;8(2):e56964. (Year: 2013).*
Extended European Search Report mailed on Nov. 10, 2021, 12 pages.
International Search Report and Written Opinion for Application No. PCT/US2019/017129, mailed on Apr. 22, 2019, 12 pages.
Dejea et al. (Feb. 2, 2018) "Patients with Familial Adenomatous Polyposis Harbor Colonic Biofilms Containing Tumorigenic Bacteria", Science, 359(6375):592-597 (7 pages).
Hernandedz-Luna et al. (Jan. 2016) "The Role of *Escherichia coli* in the Development and Progression of Cancer", ARC Journal of Cancer Science, 3(1):1-11.
Purcell et al. (Feb. 2, 2017) "Colonization with Enterotoxigenic Bacteroides Fragilis is Associated with Early-Stage Colorectal Neoplasia", PLoS One, 12(2):1-10.
Shields et al. (2016) "Reduction of Murine Colon Tumorigenesis Driven by Enterotoxigenic Bacteroides Fragilis Using Cefoxitin Treatment", the Journal of Infectious Diseases, 214:122-129.
Steele et al. (Jun. 1976) "Prevention of Low Temperature Denaturation Injury in T4Bo Phage by Low Concentrations of Traditional Cryoprotective Additives", the Journal of Hygiene, 76(3):453-458.
Bolocan et al. (Nov. 9, 2016) "Phage therapy targeting *Escherichia coli*—a story with no end?", FEMS Microbiology Letters, fnw256, 363(22):5 pages.
Budynek et al. (May 2010) "Bacteriophages and Cancer", Archives of Microbiology, 192(5):315-320.
Dabrowska et al. (2004) "Antitumor Activity of Bacteriophages in Murine Experimental Cancer Models Caused Possibly By Inhibition of [Beta]3 Integrin Signaling Pathway", Acta Virologica, 48(4):241-248.
Dabrowska et al. (2014) "Bacteriophages Displaying Anticancer Peptides in Combined Antibacterial and Anticancer Treatment", Future Microbiology, 9(7):861-869.
Dufour et al. (Nov. 1, 2016) "Bacteriophage LM33_P1, A Fast-acting Weapon Against The Pandemic ST131-025b:H4 *Escherichia Coli* Clonal Complex", J. Antimicrobial Chemotherapy, 71(11):3072-3080.
Dufour et al. (Jun. 1, 2017) "The Lysis of Pathogenic *Escherichia coli* by Bacteriophages Releases Less Endotoxin Than by β-Lactams", Clinical Infectious Diseases, 64(11):1582-1588.
Dufour et al. (Jun. 1, 2015) "Treatment of Highly Virulent Extraintestinal Pathogenic *Escherichia coli* Pneumonia With Bacteriophages", Critical Care Medicine, 43(6):29 pages.
Luo et al. (August, 2012) "Genome, Integration, and Transduction of a Novel Temperate Phage of Helicobacter pylori", Journal of Virology, 86(16):8781-8792.

(Continued)

*Primary Examiner* — Nicole Kinsey White
*Assistant Examiner* — Ruixue Wang
(74) *Attorney, Agent, or Firm* — Mintz, Levin, Cohn, Ferris, Glovsky and Popeo, P.C.

(57) ABSTRACT

The present invention relates to a bacteriophage composition comprising one or more (suitably two or more, or three) bacteriophages that target oncogenic (tumorigenic) bacteria, and use of the same for treating or preventing cancer.

24 Claims, 3 Drawing Sheets
Specification includes a Sequence Listing.

(56) References Cited

OTHER PUBLICATIONS

Uchiyama et al. (Mar. 8, 2013) "Characterization of Helicobacter pylori Bacteriophage KHP30", Applied and Environmental Microbiology, 79(10):3176-3184.

Eriksson, et al., Tumor-specific bacteriophages induce tumor destruction through activation of tumor-associated macrophages, Journal of Immunology, 2009, pp. 3105-3111, vol. 182, No. 5.

Golshahi, et al., In vitro lung delivery of bacteriophages KS4-M and ΦKZ using dry powder inhalers for treatment of Burkholderia cepacia complex and Pseudomonas aeruginosa infections in cystic fibrosis, Journal of Microbiology, 2010, pp. 106-117, vol. 110.

Hannigan, et al., Viral and Bacterial Communities of Colorectal Cancer, BioRxiv, 2017, 39 pages.

Jassim, et al., Natural solution to antibiotic resistance: bacteriophages 'The Living Drugs', World Journal of Microbiology and Biotechnology, 2014, pp. 2153-2170.

Kingwell, et al., Bacteriophage therapies re-enter clinical trials, 2015, pp. 515-516, vol. 14.

Malik, et al., Formulation, stabilization and encapsulation of bacteriophage for phage therapy, 2017, pp. 100-133, vol. 249.

Monk, et al., Bacteriophage applications: where are we now?, Letters in Applied Microbiology, 2010, pp. 363-369, vol. 51.

Pabary, et al., Antipseudomonal Bacteriophage Reduces Infective Burden and Inflammatory Response in Murine Lung, Antimicrobial Agents and Chemotherapy, 2016, pp. 744-751, vol. 60, No. 2.

Porayath, Characterization of the bacteriophages binding to human matrix molecules, International Journal of Biological Macromolecules, 2018, pp. 608-615, vol. 110.

\* cited by examiner

BACTERIOPHAGE FOR TREATMENT AND PREVENTION OF *E. COLI* AND *B. FRAGILIS* INFECTIONS

CROSS-REFERENCED APPLICATIONS

This application claims priority to U.S. Application No. 62/627,725 filed Feb. 7, 2018, the entirety of which is incorporated by reference herein.

SEQUENCE LISTING

The present disclosure contains a Sequence Listing, which has been submitted electronically in ASCII format and is hereby incorporated by reference in its entirety. The ASCII copy, created on Jan. 30, 2019, is named 054249-503001WO_Sequence_Listing_ST25 and is 1.24 megabytes in size.

FIELD

The present disclosure relates to compositions of bacteriophages, and use of the same for medical applications.

BACKGROUND

Bacterial pathogens can be associated with carcinogenesis/tumorigenesis in some tumors and/or tissues. Methods of treating or preventing cancer are needed.

SUMMARY OF THE INVENTION

The present disclosure relates to compositions and methods for treating or preventing a bacterial-associated cancer in a patient by administration of a bacteriophage composition. Preferably, the composition comprises at least one bacteriophage that targets the bacteria. The bacteriophage(s) may be specific for the bacteria or a strain (e.g., a pathogenic or carcinogenic strain) of the bacteria. Preferably, the composition minimizes development of bacterial resistance, e.g. by complementation. In some embodiments, the bacteriophages are lytic.

In an aspect, provided herein are methods for treating or preventing a bacterial-associated cancer in a patient in need thereof. The methods include administering to the patient a composition including one or more bacteriophages. In embodiments, the methods include selecting a patient with a confirmed bacterial-associated cancer. In embodiments, the bacteriophage target and lyse at least one bacterial species that is associated with cancer. In embodiments, each individual bacteriophage is not prone to generalized transduction and/or does not carry antibiotic resistance genes. In embodiments, one or more of the bacteriophages are not naturally occurring. The compositions as described herein have been shown to be efficacious in lysing bacteria associated with cancers (e.g., *E. coli*, *B. fragilis*). The bacteriophage composition can be an alternative to conventional antibacterial agents and/or cancer therapeutics, and overcomes one or more problems associated therewith. In embodiments, the bacteriophage composition can be utilized as co-treatment or in combination with conventional antibacterial agents and/or cancer therapeutics.

In an aspect, provided herein are methods for treating or preventing colorectal cancer in a patient in need thereof. In embodiments, the methods include administering to the patient a composition including one or more bacteriophages. In embodiments, the bacteriophages target at least one bacterial species that is associated with colorectal cancer. In embodiments, each individual bacteriophage is not prone to generalized transduction and/or does not carry antibiotic resistance genes. In embodiments, one or more of the bacteriophages are not naturally occurring. The compositions as described herein have been shown to be efficacious in lysing bacteria associated with colorectal cancers (e.g., *E. coli*, *B. fragilis*). The bacteriophage composition can be an alternative to conventional antibacterial agents and/or cancer therapeutics, and overcomes one or more problems associated therewith. In embodiments, the bacteriophage composition can be utilized as co-treatment or in combination with conventional antibacterial agents and/or cancer therapeutics.

In an aspect, provided herein are methods of modifying the microbial flora in a human including administering to said human a composition including one or more distinct bacteriophages having lytic activity against carcinogenic bacteria. The one or more distinct bacteriophages are selected from bacteriophages that infect *Escherichia coli*, *Bacteroides fragilis*, *Helicobacter pylori*, *Salmonella Typhi*, *Streptococcus bovis*, *Chlamydia pneumonia*, *mycoplasma*, *Helicobacter hepaticus*, and/or *Schistosoma haematobium*. In embodiments, one or more of the bacteriophage are not naturally occurring. In embodiments, the *E. coli* are positive carriers of the pks island (pks+*E. coli*). In some embodiments, the *B. fragilis* are enterotoxigenic *Bacteroides fragilis* (ETBF). The bacteriophage composition can be an alternative to conventional antibacterial agents and/or cancer therapeutics, and overcomes one or more problems associated therewith. In embodiments, the bacteriophage composition can be utilized as co-treatment or in combination with conventional antibacterial agents and/or cancer therapeutics.

In an aspect, provided herein are bacteriophage compositions including one or more obligately lytic bacteriophages that infect and lyse carcinogenic bacteria. In embodiments, the bacteriophages have a narrow spectrum of activity against the target bacterium. In embodiments, the composition is substantially free of bacterial components. In embodiments, each individual bacteriophage is not prone to generalized transduction and/or does not carry antibiotic resistance genes. In embodiments, one or more of the bacteriophages are not naturally occurring. The compositions as described herein have been shown to be efficacious in lysing bacteria associated with cancers. In embodiments, the bacteria species or strain targeted by the bacteriophages secrete a toxin that interferes with a eukaryotic cell cycle. In embodiments, the toxin is a cyclomodulin. In embodiments, the cyclomodulin is colibactin, a cyclomodulin synthesized by the pks genomic island in *E. coli*. In embodiments, the bacteria include species of *Escherichia*, *Bacteroides*, *Salmonella*, *Streptococcus*, *Chlamydia*, *mycoplasma*, *Helicobacter*, and/or *Campylobacter*. In embodiments, the bacteria species is *Escherichia coli*, *Bacteroides fragilis*, *Salmonella Typhi*, *Streptococcus bovis*, *Chlamydia pneumonia*, *Helicobacter pylori*, *Helicobacter hepaticus*, and/or *Campylobacter jejuni*. Preferably, the bacteria include *E. coli* and/or *B. fragilis*. In embodiments, the *E. coli* are pks+*E. coli*. In some embodiments, the *B. fragilis* is enterotoxigenic *Bacteroides fragilis* (ETBF). The bacteriophage composition can be an alternative to conventional antibacterial agents and/or cancer therapeutics, and overcomes one or more problems associated therewith. In embodiments, the bacteriophage composition can be utilized as co-treatment or in combination with conventional antibacterial agents and/or cancer therapeutics.

In an aspect, provided herein is a bacteriophage composition that includes one or more bacteriophages that target a carcinogenic bacteria, and a cryoprotectant. In embodiments, the composition is substantially free of bacterial components. In embodiments, each individual bacteriophage is not prone to generalized transduction and/or does not carry antibiotic resistance genes. In embodiments, one or more of the bacteriophages are not naturally occurring. The compositions as described herein have been shown to be efficacious in lysing bacteria associated with cancers. In embodiments, the bacteria species or strain targeted by the bacteriophages secrete a toxin that interferes with a eukaryotic cell cycle. In embodiments, the toxin is a cyclomodulin. In embodiments, the cyclomodulin is colibactin, a cyclomodulin synthesized by the pks genomic island in *E. coli*. In embodiments, the bacteria include species of *Escherichia, Bacteroides, Salmonella, Streptococcus, Chlamydia, mycoplasma, Helicobacter*, and/or *Campylobacter*. In embodiments, the bacteria species is *Escherichia coli, Bacteroides fragilis, Salmonella Typhi, Streptococcus bovis, Chlamydia pneumonia, Helicobacter pylori, Helicobacter hepaticus*, and/or *Campylobacter jejuni*. Preferably, the bacteria include *E. coli* and/or *B. fragilis*. In embodiments, the *E. coli* are pks+*E. coli*. In some embodiments, the *B. fragilis* is enterotoxigenic *Bacteroides fragilis* (ETBF). The bacteriophage composition can be an alternative to conventional antibacterial agents and/or cancer therapeutics, and overcomes one or more problems associated therewith. In embodiments, the bacteriophage composition can be utilized as co-treatment or in combination with conventional antibacterial agents and/or cancer therapeutics.

In an aspect, provided herein are bacteriophage compositions for use in treating a bacterial associated cancer in a subject. The methods include selecting a patient with a bacterial-associated cancer and administering a bacteriophage composition. In embodiments, the cancer may be any cancer that is caused by or associated with infection by a bacteria or bacteria strain. In embodiments, the bacterial-associated cancer is colorectal cancer, esophageal cancer, gallbladder cancer, lung cancer, squamous cell carcinoma, bladder cancer, stomach cancer, or mucosa-associated lymphoid tissue (MALT) lymphoma.

In an aspect, provided herein are uses of any composition described herein in the treatment of a confirmed bacterial-associated cancer. The uses include treatment of bacterial-associated cancer including administration to said human of a composition, the composition comprising at least one bacteriophage that targets and lyses a bacteria associated with cancer. In embodiments, the composition is substantially free of bacterial components. In embodiments, each individual bacteriophage is not prone to generalized transduction and/or does not carry antibiotic resistance genes. In embodiments, one or more of the bacteriophages are not naturally occurring. The compositions as described herein have been shown to be efficacious in lysing bacteria associated with cancers. In embodiments, the bacteria species or strain targeted by the bacteriophages secrete a toxin that interferes with a eukaryotic cell cycle. In embodiments, the toxin is a cyclomodulin. In embodiments, the cyclomodulin is colibactin, a cyclomodulin synthesized by the pks genomic island in *E. coli*. In embodiments, the bacteria include species of *Escherichia, Bacteroides, Salmonella, Streptococcus, Chlamydia, mycoplasma, Helicobacter*, and/or *Campylobacter*. In embodiments, the bacteria species is *Escherichia coli, Bacteroides fragilis*), *Salmonella Typhi, Streptococcus bovis, Chlamydia pneumonia, Helicobacter pylori, Helicobacter hepaticus*, and/or Campylobacterjejuni. Preferably, the bacteria include *E. coli* and/or *B. fragilis*. In embodiments, the *E. coli* are pks+*E. coli*. In some embodiments, the *B. fragilis* is enterotoxigenic *Bacteroides fragilis* (ETBF). The bacteriophage composition can be an alternative to conventional antibacterial agents and/or cancer therapeutics, and overcomes one or more problems associated therewith. In embodiments, the bacteriophage composition can be utilized as co-treatment or in combination with conventional antibacterial agents and/or cancer therapeutics.

In an aspect, provided herein is a kit that includes a bacteriophage composition and instructions for use of the same.

DETAILED DESCRIPTION

Figure 1:
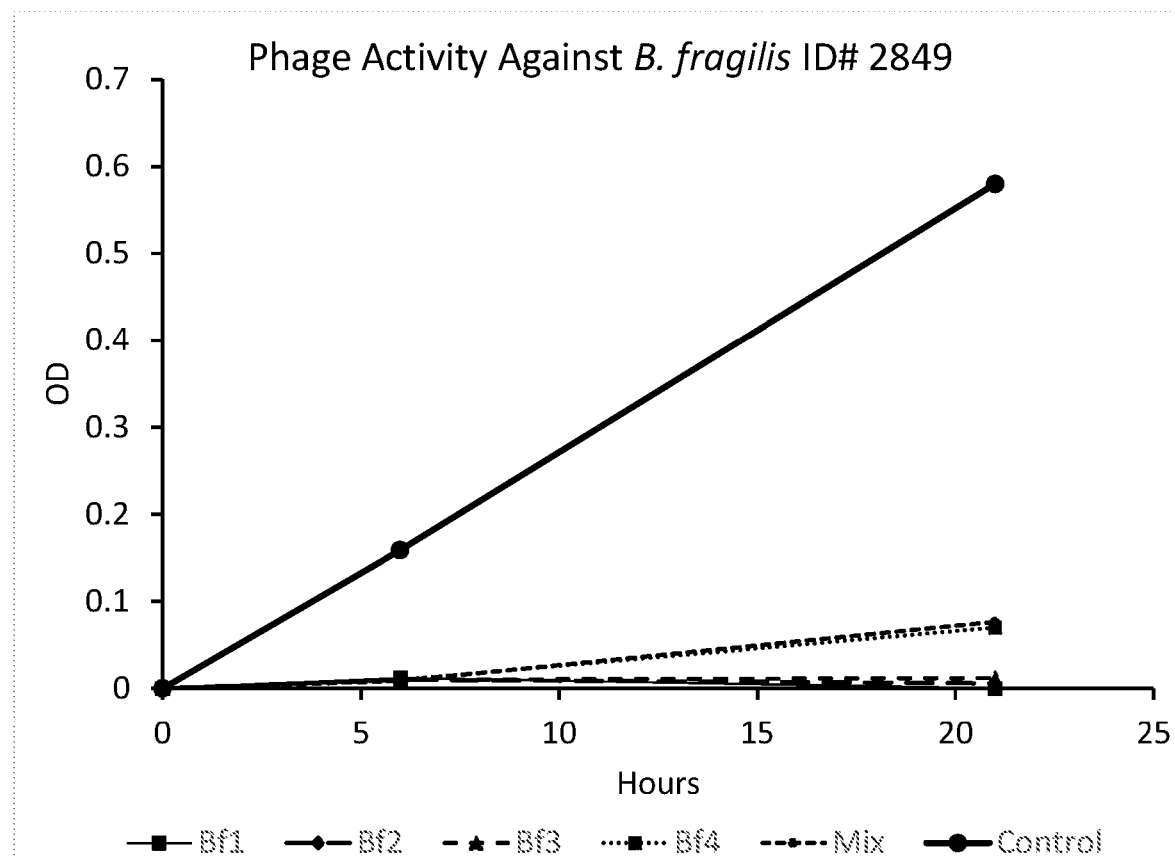
FIG. 1 is a graph of phage activity of four different phage and a mixture of phage against a *Bacteroides fragilis* strain (Clindamycin resistant).

The invention is predicated upon the surprising finding by the present inventors that a bacteriophage composition comprising one or more (preferably at least two) bacteriophages selected from phages that infect and lyse carcinogenic bacteria, or mutants thereof, is particularly advantageous for use in both medical and non-medical applications such as a rapid companion diagnostic, and particularly for treating a bacterial associated cancer in a subject.

It is to be understood that the present disclosure is not limited to particular embodiments described, as such may, of course, vary. It is also to be understood that the terminology used herein is for describing particular embodiments only, and is not intended to be limiting, since the scope of the present disclosure will be limited only by the appended claims.

The detailed description of the present disclosure is divided into various sections only for the reader's convenience and disclosure found in any section may be combined with that in another section. Unless defined otherwise, all technical and scientific terms used herein have the same meaning as commonly understood by one of ordinary skill in the art to which the present disclosure belongs.

Definitions

It must be noted that as used herein and in the appended claims, the singular forms "a," "an," and "the" include plural referents unless the context clearly dictates otherwise. Thus, for example, reference to "a bacteriophage composition" includes a plurality of such candidate agents and reference to "the bacteriophage" includes reference to one or more bacteriophages and equivalents thereof known to those skilled in the art, and so forth.

As used herein, the term "about" when used before a numerical designation, e.g., temperature, time, amount, concentration, and such other, including a range, indicates approximations which may vary by (+) or (−) 10%, 5%, or 1%.

When a range (e.g., dosage range) is listed herein, it is to be understood that the value may include any value or range within the recited range(s), including endpoints.

The term "mutant" as used herein refers to a bacteriophage differing genetically from a particular bacteriophage by one or more nucleotides while retaining the ability to infect and lyse target bacteria. Mutants typically comprise e.g., silent mutations, conservative mutations, minor deletions, and/or minor replications of genetic material, and retain phenotypic characteristics of the reference bacteriophage. In a preferred embodiment, the mutants of the invention retain any observable characteristic or property that is dependent upon the genome of the bacteriophage of the invention, i.e. phenotypic characteristics of said bacteriophage and/or activity against the bacteria strains. Preferred mutants have less than 5% nucleic acid variation as compared to the genome of the reference bacteriophage, even more preferably less than 4%, more preferably less than 2%. Alternatively, or in combination, mutants have preferably less than 5% amino acid variation in a coded polypeptide sequence as compared to a polypeptide of the reference bacteriophage.

The term "% identity" or "% sequence identity" in relation to nucleic acid or amino acid sequences designates the level of identity or homology between said sequences and may be determined by techniques known per se in the art. Any of a variety of sequence alignment methods can be used to determine percent identity, including, without limitation, global methods, local methods and hybrid methods, such as segment approach methods. Protocols to determine percent identity are routine procedures within the scope of one skilled in the art. Global methods align sequences from the beginning to the end of the molecule and determine the best alignment by adding up scores of individual nucleotide pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) *Nucleic Acids Research* 4673-4680 (1994); and iterative refinement. Non-limiting methods include, e.g., BLAST, Match-box, see, e.g., Align-M, see, e.g., Ivo Van Walle et al., Align-M—A New Algorithm for Multiple Alignment of Highly Divergent Sequences, 20(9) *Bioinformatics* 1428-1435 (2004).

The term "complementation" as used herein refers to the ability of a bacteriophage with a particular genome to compensate for a different, distinct bacteriophage with a different genome. More specifically, bacteriophage insensitive mutant colonies (of target bacteria) may arise to a particular bacteriophage but may still be sensitive to a different bacteriophage. In other words, bacteriophage-resistant mutant bacteria arising to one phage are still sensitive to another phage.

The term "generalized transduction" as used herein refers to the process by which bacterial DNA may be transferred to another bacterium via a bacteriophage. It is a rare event; a very small percentage of phage particles happen to carry a donor bacterium's DNA, on the order of 1 phage in 10,000. In essence, this is the packaging of bacterial DNA into a viral capsid.

The term "lytic" or "lytic activity" designates the property of a bacteriophage to cause lysis of a bacterial cell. The lytic activity of a bacteriophage can be tested on bacteria (e.g., *E. coli* strains) according to techniques known in the art. The lytic cycle is named for the process that occurs when a phage has infected a cell, replicated new phage particles, and bursts through the host cell wall and membrane(s). Some phage exhibit a lysogenic cycle during which the bacteriophage DNA remains practically dormant due to active repression of bacteriophage processes. Whenever the bacteria divides, the DNA of the phage is copied as well. In this way, the virus can continue existing within its host without lysing the host. At a certain point, conditions may change and the phage enters a lytic cycle. "Obligately lytic" refers to phage that are unable to undergo a lysogenic cycle.

Non-limiting examples of *E. coli* bacteriophages include EC200pp (Bolocan et al, FEMS Microbiology Letters, Vol. 363, Issue 22, Nov. 1, 2016), LM33-P1 (Dufour et al, J. Antimicrobial Chemotherapy, Vol. 71, Issue 11, Nov. 1, 2016, p 3072-3080), 536_P1 (Dufour et al, Clinical Infectious Diseases, Vol. 64, Issue 11, June 2017, p 1589-1590), 536_P7 (Dufour et al, Critical Care Medicine, 43(6):e190-e198, June 2015), T4, Lamda Argo2, Lambda Argo 1, T3, P1, PR722, Ox6, Lamda W60, rEDb44, r1589, T6, rA105, r71, UV1, 49B, BG3, 53 alpha, rEDb50, 221, Phi X174, 184, rH23, r638, r187, rJ3, rED220, FCZ, r196, rEDb45, rH88, 547, C204, 24B, 6C, rEDa41, UV47, G178, C33, T2, and T1 (ATCC collection). Non-limiting examples of *Bacteroides fragilis* bacteriophages include B40-8 (RefSeq: NC_011222), B124-14 (RefSeq: NC_016770), 51477-B1 (ATCC.org). Non-limiting examples of *Salmonella Typhi* bacteriophages include phSE-1, phSE-2, phSE-5 (Pereira et al, Virus Res., 2016 Jul. 15; 220:179-92). Non-limiting examples of *Streptococcus bovis* bacteriophages include the phages isolated and characterized by Iverson et al (Iverson et al, Canadian Journal of Microbiology, 1976, 22(6):847-852). Non-limiting examples of *Chlamydia pneumonia* bacteriophages include φCPAR39 (Hoestgaard-Jensen et al, FEMS Immunology & Medical Microbiology, Vol. 62, Issue 2, Jul. 1, 2011, p 148-156). Non-limiting examples of *Helicobacter* bacteriophages include KHP30 (Uchiyama et al, Appl. Environ. Microbiol. April 2013, 79(10) 3176-3184), HP1 (Heintschel et al, J. Med. Microbiol., Apr. 1, 1993, 38:245-249), 1961P (Luo et al, Journal of Virology, July 2012, 86 (16) 8781-8792). Non-limiting examples of *Campylobacter jejuni* bacteriophages include CP8 and CP34 (Loc Carrillo et al, Appl. Environ. Microbiol., November 2005, 71(11) 6554-6563), c/958 (Ritchie et al, J. Med. Microbiol., Vol 16, 1983, 333-340), phages 1-14 identified by Grajewski et al (Grajewski et al, Journal of Clinical Microbiology, July 1985, p 13-18). In embodiments, compositions and methods provided herein exclude one or more bacteriophage described herein.

The term "treat" or "treating" as used herein is intended to encompass prophylactic treatment as well as corrective treatment (treatment of a subject already suffering from a disease). Treating may also refer to treating one or more symptoms of a disease or disorder, as well as slowing or stopping progression of the disease or disorder.

The term "prevent" or "preventing" as used herein is intended to encompass preventing a disease or disorder (e.g., cancer) from occurring in a patient or patient population, as well as reducing the occurrence of the disease or disorder, slowing/prolonging the onset of the disease or disorder, and the like.

The term "bacterial-associated cancer," "carcinogenic bacteria," and "tumorigenic bacteria" refer to infectious organisms that are known or suspected to cause cancer. While cancer-associated bacteria have been considered to be opportunistic (i.e., infecting healthy tissues after cancer has already established itself), there is evidence that bacteria may be directly carcinogenic. The complex relationship between bacteria and humans is demonstrated by *Helico-*

*bacter pylori* and *Salmonella Typhi* infections. Research has shown that *H. pylori* can cause gastric cancer or MALT lymphoma in some individuals. *Salmonella Typhi* infection has been associated with the development of gallbladder cancer. Many species, however, share an important characteristic: highly site-specific colonization.

A use or method of the invention typically comprises administering a bacteriophage composition described herein to a subject or patient. As used herein, a "subject" or "patient" is a mammal, such as a human or other animal. Preferably, the subject or patient is a human. Preferably, the subject or patient is in need of treatment with the composition as described herein, e.g., has a bacterial infection susceptible to treatment with the composition.

The term "isolated" as used herein indicates that the bacteriophage is removed from the environment in which it naturally occurs. In particular, an isolated bacteriophage is, e.g., cultivated, cultured separately from the environment in which it is naturally located. Some aspects herein relate to isolated bacteriophage (individually and/or collectively), compositions of the same, and methods of using the same to treat bacteria associated cancers. The isolated bacteriophage include, but are not limited to, those specifically described and listed herein.

The term "purified" as used herein indicates that the bacteriophage are removed from manufacturing host bacteria. In particular, a purified bacteriophage has production impurities, such as bacterial components, removed from its manufacturing or production environment. Bacterial components include but are not limited to bacterial host proteins, lipids, and/or bacterial endotoxin. The term "purified" may also refer to genetic purification in which the strain of bacteriophage is genetically homogenous. Some aspects herein relate to purified bacteriophage (individually and/or collectively), compositions of the same, and methods of using the same to treat bacteria associated cancers. The purified bacteriophage include, but are not limited to, those specifically described and listed herein.

As used herein, the term "substantially purified" refers to a composition containing less than 1%, less than 0.1%, less than 0.001%, or no detectable amount of contaminants such as host bacterial proteins or endotoxin. Also, as used herein, the term "substantially pure" when used to describe a bacteriophage strain refers to the genetic purity of the composition such that the consensus sequence of each phage within the composition is greater than 99%, greater than 99.9%, greater than 99.999%, or 100% identical to the expected nucleic acid sequence for that phage. Some aspects herein relate to substantially purified bacteriophage (individually and/or collectively), compositions of the same, and methods of using the same to treat bacteria associated cancers. The substantially purified bacteriophage include, but are not limited to, those specifically described and listed herein.

Typically, a composition is substantially pure when at least 80%, more preferably at least 85%, more preferably at least 90%, more preferably at least 95%, more preferably at least 98%, and most preferably at least 99% of the total material (by volume, by wet or dry weight, or by mole percent or mole fraction) in a sample is free of impurities and/or genetic variants.

The term "substantially free" as used herein can refer to something having less than 10% of the substance that it is to be free from. For example, 0.01% to 10% free, including any subvalue and subrange therein, including endpoints. For example, 0.01, 0.02, 0.03, 0.04, 0.05, 0.06, 0.07, 0.08, 0.09, 1, 2, 3, 4, 5, 6, 7, 8, 9, or 10%.

A "synergistic amount" as used herein refers to the sum of a first amount (e.g., a bacteriophage) and a second amount (e.g., a different bacteriophage) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent.

The term "consists essentially of" as used herein means that only the bacteriophage(s) explicitly indicated are present in the bacteriophage composition, but that said composition may also contain a further non-bacteriophage constituent, such as an appropriate carrier, diluent, antibiotic (e.g., chemical antibiotic), etc.

Additional terms and phrases are defined below.

Bacteriophage Compositions

Provided herein are bacteriophage compositions, including compositions that are substantially free of bacterial components such as for example bacterial endotoxins, bacterial host protein, and the like. The compositions can include one or more obligately lytic bacteriophages and optionally a cryoprotectant. The bacteriophage can be any phage as described herein, and may include at least one phage with a nucleic acid sequence or a genome including a nucleotide sequence having at least 90% identity to any one of SEQ ID NO: 1-6. The bacteriophage can be any phage as described herein, and may include at least one phage with a nucleic acid sequence or a genome including a nucleotide sequence having at least 90% identity to the genomic sequence of deposited strain Bf1 (Accession No. 040219-02), Bf2 (Accession No. 040219-03), Bf3 (Accession No. 040219-04), and/or Bf4 (Accession No. 040219-05) deposited at the Canadian Science Centre for Human and Animal Health. In some aspects at least one of the bacteriophage do not have 100% identity to one or more of SEQ ID NO: 1, SEQ ID NO: 2, SEQ ID NO: 3, SEQ ID NO: 4, SEQ ID NO: 5, SEQ ID NO: 6. In some aspects at least one of the bacteriophage do not have 100% identity to one or more of the genomic sequence of deposited strain Bf1 (Accession No. 040219-02), Bf2 (Accession No. 040219-03), Bf3 (Accession No. 040219-04), and/or Bf4 (Accession No. 040219-05) deposited at the Canadian Science Centre for Human and Animal Health (International Depository of Canada). In some aspects one or more of the bacteriophage are non-naturally occurring. In some aspects, an individual bacteriophage is not prone to generalized transduction and/or does not carry antibiotic resistance genes. In embodiments, compositions and methods provided herein exclude one or more bacteriophage described herein.

Provided herein are bacteriophage compositions including one or more bacteriophage that infect and lyse carcinogenic bacteria. In embodiments, the bacteriophage have a narrow spectrum of action against the target bacterium. In embodiments, one or more of the bacteriophage are not naturally occurring. In embodiments, the composition is substantially free of bacterial components. In embodiments, each individual bacteriophage is not prone to generalized transduction and/or does not carry antibiotic resistance genes.

In embodiments, the bacteriophage differ in nucleotide or genomic sequence by up to about 15%, up to about 14%, up to about 13%, up to about 12%, up to about 11%, up to about 10%, up to about 9%, up to about 8%, up to about 7%, up to about 6%, up to about 5%, up to about 4%, up to about 3%, up to about 2%, or up to about 1% compared to the genomic sequence of *E. coli* phage Ec20 (SEQ ID NO: 1), Ec34 (SEQ ID NO: 2), Ec35 (SEQ ID NO: 3), Ec45 (SEQ ID NO: 4), Ec56 (SEQ ID NO: 5) and/or Ec57 (SEQ ID NO: 6). In embodiments, the bacteriophage differ in nucleotide or genomic sequence by up to about 15%, up to about 14%, up to about 13%, up to about 12%, up to about 11%, up to about 10%, up to about 9%, up to about 8%, up to about 7%, up to about 6%, up to about 5%, up to about 4%, up to about 3%, up to about 2%, or up to about 1% compared to the genomic sequence of *B. fragilis* phage Bf1 (Accession No. 040219-02), Bf2 (Accession No. 040219-03), Bf3 (Accession No. 040219-04), and/or Bf4 (Accession No. 040219-05) deposited at the Canadian Science Centre for Human and Animal Health (International Depository of Canada).

The compositions as described herein have been shown to be particularly useful in for treating bacterial infections, in particular bacteria associated with cancers. As used herein, the terms "oncogenic bacteria", "tumorigenic bacteria", and "bacteria associated with cancers" are used interchangeable. In embodiments, the bacteriophages precisely target the tumorigenic bacteria without broadly destroying microbiota (e.g., other bacteria and/or microbes) present in the patient. In embodiments, the bacteriophages are specific for tumorigenic bacteria and do not target other microorganisms.

In embodiments, the bacteria include *Escherichia coli, Bacteroides* species (e.g., *Bacteroides fragilis*), *Salmonella Typhi, Streptococcus bovis, Chlamydia pneumonia, mycoplasma, Helicobacter* species (e.g., *Helicobacter pylori, Helicobacter hepaticus*), and/or *Campylobacter jejuni*. In embodiments, the bacteria include *E. coli* and/or *B. fragilis*. In embodiments, the *E. coli* are pks+*E. coli*. In some embodiments, the *B. fragilis* are enterotoxigenic *Bacteroides fragilis* (ETBF). In one embodiment, the *B. fragilis* is a Clindamycin resistant strain. In one embodiment, the *B. fragilis* is a Clindamycin sensitive strain. In embodiments, the bacteria species or strain targeted by the bacteriophages secrete a toxin that interferes with a eukaryotic cell cycle. In embodiments, the toxin is a cyclomodulin. In embodiments, the cyclomodulin is colibactin, a cyclomodulin synthesized by the pks genomic island in *E. coli*.

In embodiments, the bacteriophage composition includes at least one, at least two, at least three, or at least four bacteriophages such that the composition is effective against at least about 60% of target bacterial strains. For example, the bacteriophage composition is effective against (e.g., kills or lyses) at least 60% of *E. coli* and/or *B. fragilis* strains in a given panel. In one embodiment, the bacteriophage composition includes at least one, at least two, at least three, or at least four bacteriophages such that the composition is effective against at least about 70% of target bacterial strains. In one embodiment, the bacteriophage composition includes at least one, at least two, at least three, or at least four bacteriophages such that the composition is effective against at least about 75% of target bacterial strains. In one embodiment, the bacteriophage composition includes at least one, at least two, at least three, or at least four bacteriophage such that the composition is effective against at least about 76% of target bacterial strains. In one embodiment, the bacteriophage composition includes at least one, at least two, at least three, or at least four bacteriophages such that the composition is effective against at least about 77% of target bacterial strains. In one embodiment, the bacteriophage composition comprises at least one, at least two, at least three, or at least four bacteriophages such that the composition is effective against at least about 78% of target bacterial strains. In one embodiment, the bacteriophage composition includes at least one, at least two, at least three, or at least four bacteriophages such that the composition is effective against at least about 79% of target bacterial strains. In one embodiment, the bacteriophage composition includes at least one, at least two, at least three, or at least four bacteriophages such that the composition is effective against at least about 80% of target bacterial strains. In one embodiment, the bacteriophage composition includes at least one, at least two, at least three, or at least four bacteriophages such that the composition is effective against at least about 81% of target bacterial strains. In one embodiment, the bacteriophage composition includes at least one, at least two, at least three, or at least four bacteriophages such that the composition is effective against at least about 82% of target bacterial strains. In one embodiment, the bacteriophage composition includes at least one, at least two, at least three, or at least four bacteriophage such that the composition is effective against at least about 83% of target bacterial strains. In one embodiment, the bacteriophage composition includes at least one, at least two, at least three, or at least four bacteriophages such that the composition is effective against at least about 84% of target bacterial strains. In one embodiment, the bacteriophage composition includes at least one, at least two, at least three, or at least four bacteriophage such that the composition is effective against at least about 85% of target bacterial strains. In one embodiment, the bacteriophage composition includes at least one, at least two, at least three, or at least four bacteriophage such that the composition is effective against at least about 90% of target bacterial strains. In another embodiment, the bacteriophage composition includes at least one, at least two, at least three, or at least four bacteriophages such that the composition is effective against one or more bacterial strains (or isolates) from a subject with a bacterial infection.

In embodiments, the bacteria or bacteria strain targeted by the bacteriophages are associated with cancer. In embodiments, the bacteria species or strain targeted by the bacteriophages secrete a toxin that interferes with a eukaryotic cell cycle. In embodiments, the toxin is a cyclomodulin. In embodiments, the cyclomodulin is colibactin, a cyclomodulin synthesized by the pks genomic island in *E. coli*. In embodiments, the bacteria include *Escherichia coli, Bacteroides* species (e.g., *Bacteroides fragilis*), *Salmonella Typhi, Streptococcus bovis, Chlamydia pneumonia, mycoplasma, Helicobacter* species (e.g., *Helicobacter pylori, Helicobacter hepaticus*), and/or *Campylobacter jejuni*. Preferably, the bacteria include *E. coli* and/or *B. fragilis*. In embodiments, the *E. coli* are pks+*E. coli*. In some embodiments, the *B. fragilis* are enterotoxigenic *Bacteroides fragilis* (ETBF). In one embodiment, the *B. fragilis* is a Clindamycin resistant strain. In one embodiment, the *B. fragilis* is a Clindamycin sensitive strain.

In embodiments, the bacteriophage compositions comprise at least one bacteriophage that targets an oncogenic bacteria or bacterial strain, or mutants of such bacteriophages. In one embodiment, a bacteriophage composition comprises at least two bacteriophages or mutants thereof. In one embodiment, a bacteriophage composition comprises at least three bacteriophages or mutants thereof. In one embodiment, the bacteriophage composition comprises one or more additional bacteriophages, for example one or more additional bacteriophages that target a different bacteria or bacteria strain. In a preferred embodiment, the one or more additional bacteriophages are suitable for treating an oncogenic bacterial infection.

The bacteriophages may be of any type that are capable of infecting/targeting the target bacterial strain or species. In embodiments, the bacteriophages are capable of lysing the target bacterial species or strain.

In embodiments (alternatively or additionally), a "mutant" bacteriophage is capable of lysing the same target bacterial strains as the parent bacteriophage, and further capable of lysing one or more additional bacterial strains. In one embodiment a mutant may have at least 75%, 80%, 85%, 86%, 87%, 88%, 89%, 90%, 91%, 92%, 93%, 94%, 95%, 96%, 97%, 98%, or 99% sequence identity across its entire genome when compared to the parent bacteriophage.

In embodiments, the bacteriophage composition targets one or more *Escherichia* species. In embodiments, the bacteriophage composition targets one or more *E. coli* strains (e.g., one or more oncogenic *E. coli* strains). In one embodiment, an *E. coli* strain targeted is a colibactin-producing strain. In one embodiment, an *E. coli* strain targeted is a pks+*E. coli* strain. See, for example, Dejea et al., Science 359, 592-597 (2018), which is incorporated herein by reference in its entirety. In embodiments, the composition includes one or more bacteriophage selected from Ec20, Ec34, Ec35, Ec45, Ec56, and Ec57. In embodiments, the composition includes two bacteriophage selected from Ec20, Ec34, Ec35, Ec45, Ec56, and Ec57. In embodiments, the composition includes three bacteriophage selected from Ec20, Ec34, Ec35, Ec45, Ec56, and Ec57. In embodiments, the composition includes four bacteriophage selected from Ec20, Ec34, Ec35, Ec45, Ec56, and Ec57. In embodiments, the composition includes five bacteriophage selected from Ec20, Ec34, Ec35, Ec45, Ec56, and Ec57. In embodiments, the composition includes six bacteriophage selected from Ec20, Ec34, Ec35, Ec45, Ec56, and Ec57. In one embodiment, the bacteriophage are Ec34 (Accession No. 040219-07), Ec35 (Accession No. 040219-08), Ec45 (Accession No. 040219-09), and Ec57 (Accession No. 040219-10) deposited at the Canadian Science Centre for Human and Animal Health (International Depository of Canada). In one embodiment, the bacteriophage are Ec34 (Accession No. 040219-07), Ec35 (Accession No. 040219-08), and Ec57 (Accession No. 040219-10) deposited at the Canadian Science Centre for Human and Animal Health (International Depository of Canada). In embodiments, compositions provided herein exclude one or more bacteriophage described herein.

In embodiments, the bacteriophage composition targets one or more *Bacteroides* species. In embodiments, the bacteriophage composition targets one or more *B. fragilis* strains (e.g., one or more oncogenic *B. fragilis* strains). In one embodiment, a *B. fragilis* strain targeted is a *Bacteroides fragilis* toxin (bft)-producing strain. In one embodiment, the *Bacteroides fragilis* strain targeted is an enterotoxigenic *Bacteroides fragilis* (ETBF) strain. In one embodiment, the *B. fragilis* is a Clindamycin resistant strain. In one embodiment, the *B. fragilis* is a Clindamycin sensitive strain. In embodiments, provided herein are bacteriophages known to target *Bacteroides fragilis* including Bf1 (Accession No. 040219-02), Bf2 (Accession No. 040219-03), Bf3 (Accession No. 040219-04), and/or Bf4 (Accession No. 040219-05) deposited at the Canadian Science Centre for Human and Animal Health (International Depository of Canada). In embodiments, the composition includes one or more bacteriophage selected from Bf1, Bf2, Bf3, and Bf4. In embodiments, the composition includes two bacteriophage selected from Bf1, Bf2, Bf3, and Bf4. In embodiments, the composition includes three bacteriophage selected from Bf1, Bf2, Bf3, and Bf4. In embodiments, the composition includes bacteriophage Bf1, Bf2, Bf3, and Bf4. In embodiments, compositions provided herein exclude one or more bacteriophage described herein.

In one embodiment, the bacteriophage composition targets one or more *Salmonella* species. In one embodiment, the bacteriophage composition targets one or more *Salmonella Typhi* strains. In embodiments, provided herein are bacteriophages known to target *Salmonella Typhi* including bacteriophage phSE-1, phSE-2, and phSE-5. In embodiments, compositions provided herein exclude one or more bacteriophage described herein.

In embodiments, the bacteriophage composition targets one or more *Streptococcus* species. In embodiments, the bacteriophage composition targets one or more *Streptococcus bovis* strains. In embodiments, provided herein are bacteriophages known to target *Streptococcus bovis* including the phages isolated and characterized by Iverson et al (Iverson et al, Canadian Journal of Microbiology, 1976, 22(6):847-852). In embodiments, compositions provided herein exclude one or more bacteriophage described herein.

In embodiments, the bacteriophage composition targets one or more *Chlamydia* species. In one embodiment, the bacteriophage composition targets one or more *Chlamydia* pneumonia strains. In embodiments, provided herein are bacteriophages known to target *Chlamydia* pneumonia including bacteriophage φCPAR39. In embodiments, compositions provided herein exclude one or more bacteriophage described herein.

In embodiments, the bacteriophage composition targets one or more *mycoplasma* species e.g. *M. hominis, M. genitalium, M. fermentans,* M. pneuomonia, and *M. mycoides*. In embodiments, the bacteriophage composition targets one or more *mycoplasma* strains. In embodiments, provided herein are bacteriophages known to target *mycoplasma*, including bacteriophage phiMFV1 and MAV1. In embodiments, compositions provided herein exclude one or more bacteriophage described herein.

In embodiments, the bacteriophage composition targets one or more *Helicobacter* species (e.g., *Helicobacter pylori, Helicobacter hepaticus*). In embodiments, the bacteriophage composition targets one or more *Helicobacter pylori* strains. In embodiments, the bacteriophage composition targets one or more *Helicobacter hepaticus* strains. In embodiments, provided herein are bacteriophages known to target *Helicobacter* including bacteriophage KHP30, HP1, and 1961P. In embodiments, compositions provided herein exclude one or more bacteriophage described herein.

In embodiments, the bacteriophage composition targets one or more *Campylobacter* species. In embodiments, the bacteriophage composition targets one or more *Campylobacter jejuni* strains. In embodiments, provided herein are bacteriophages known to target *Campylobacter jejuni* including bacteriophage CP8, CP34, and c/958. In embodiments, compositions provided herein exclude one or more bacteriophage described herein.

The bacteriophages Ec34 (Accession No. 040219-07), Ec35 (Accession No. 040219-08), Ec45 (Accession No. 040219-09), and Ec57 (Accession No. 040219-10) were deposited at the Canadian Science Centre for Human and Animal Health (International Depository of Canada). All of the deposits were made under the provisions of the Budapest Treaty on the International Recognition of the Deposit of Microorganisms for the Purposes of Patent Procedure.

The bacteriophages Bf1 (Accession No. 040219-02), Bf2 (Accession No. 040219-03), Bf3 (Accession No. 040219-04), and/or Bf4 (Accession No. 040219-05) deposited at the Canadian Science Centre for Human and Animal Health (International Depository of Canada). All of the deposits were made under the provisions of the Budapest Treaty on the International Recognition of the Deposit of Microorganisms for the Purposes of Patent Procedure.

In embodiments, compositions provided herein include one or more bacteriophage selected from Ec20, Ec34, Ec35, Ec45, Ec56, Ec57, Bf1, Bf2, Bf3, and Bf4. In embodiments, the composition includes two bacteriophage selected from Ec20, Ec34, Ec35, Ec45, Ec56, Ec57, Bf1, Bf2, Bf3, and Bf4. In embodiments, the composition includes three bacteriophage selected from Ec20, Ec34, Ec35, Ec45, Ec56, Ec57, Bf1, Bf2, Bf3, and Bf4. In embodiments, the composition includes four bacteriophage selected from Ec20, Ec34, Ec35, Ec45, Ec56, Ec57, Bf1, Bf2, Bf3, and Bf4. In embodiments, the composition includes five bacteriophage selected from Ec20, Ec34, Ec35, Ec45, Ec56, Ec57, Bf1, Bf2, Bf3, and Bf4. In embodiments, the composition includes six bacteriophage selected from Ec20, Ec34, Ec35, Ec45, Ec56, Ec57, Bf1, Bf2, Bf3, and Bf4. In embodiments, the composition includes seven bacteriophage selected from Ec20, Ec34, Ec35, Ec45, Ec56, Ec57, Bf1, Bf2, Bf3, and Bf4. In embodiments, the composition includes eight bacteriophage selected from Ec20, Ec34, Ec35, Ec45, Ec56, Ec57, Bf1, Bf2, Bf3, and Bf4. In embodiments, the composition includes nine bacteriophage selected from Ec20, Ec34, Ec35, Ec45, Ec56, Ec57, Bf1, Bf2, Bf3, and Bf4. In embodiments, the composition includes ten bacteriophage selected from Ec20, Ec34, Ec35, Ec45, Ec56, Ec57, Bf1, Bf2, Bf3, and Bf4. In embodiments, the composition includes Ec34, Ec35, Ec45, Ec57, Bf1, Bf2, Bf3, and Bf4. In embodiments, compositions provided herein exclude one or more bacteriophage described herein.

The bacteriophages of a composition of the invention may be provided in the form of a single therapeutic composition (preferred) or as a number of separate compositions each comprising one or more members of the composition. In embodiments where the bacteriophages are provided in a number of separate compositions, said bacteriophages may be administered to a subject sequentially or simultaneously.

In embodiments where more than one bacteriophage is present in the bacteriophage composition, the composition is formulated such that each bacteriophage may be present at a ratio of between 1:10 and 10:1 (or any sub value or subrange there between including the endpoints) compared to the amount (e.g., concentration) of any other bacteriophage in the composition. In embodiments, each bacteriophage is present at a ratio of about 1:1 compared to one or more other bacteriophages in the composition. In embodiments, each bacteriophage is present at a ratio of about 1:2 compared to one or more other bacteriophages in the composition. In embodiments, each bacteriophage is present at a ratio of about 1:3 compared to one or more other bacteriophages in the composition. In embodiments, each bacteriophage is present at a ratio of about 1:4 compared to one or more other bacteriophages in the composition. In embodiments, each bacteriophage is present at a ratio of about 1:5 compared to one or more other bacteriophages in the composition. In embodiments, each bacteriophage is present at a ratio of about 1:6 compared to one or more other bacteriophages in the composition. In embodiments, each bacteriophage is present at a ratio of about 1:7 compared to one or more other bacteriophages in the composition. In embodiments, each bacteriophage is present at a ratio of about 1:8 compared to one or more other bacteriophages in the composition. In embodiments, each bacteriophage is present at a ratio of about 1:9 compared to one or more other bacteriophages in the composition. In embodiments, each bacteriophage is present at a ratio of about 1:10 compared to one or more other bacteriophages in the composition. In embodiments, each bacteriophage is present at a ratio of about 10:1 compared to one or more other bacteriophages in the composition. In embodiments, each bacteriophage is present at a ratio of about 5:1 compared to one or more other bacteriophages in the composition. In embodiments, each bacteriophage is present at a ratio of about 10:3 compared to one or more other bacteriophages in the composition. In embodiments, each bacteriophage is present at a ratio of about 5:2 compared to one or more other bacteriophages in the composition. In embodiments, each bacteriophage is present at a ratio of about 2:1 compared to one or more other bacteriophages in the composition. In embodiments, each bacteriophage is present at a ratio of about 5:3 compared to one or more other bacteriophages in the composition. In embodiments, each bacteriophage is present at a ratio of about 10:7 compared to one or more other bacteriophages in the composition. In embodiments, each bacteriophage is present at a ratio of about 5:4 compared to one or more other bacteriophages in the composition.

A bacteriophage for inclusion in a composition may be propagated by any suitable method known in the art. For example, one or more bacteriophage(s) may be grown separately in host bacterial strains capable of supporting growth of the bacteriophage. Typically, the bacteriophage will be grown in said host bacterial strain to high concentrations, titrated and combined to form the composition. The amount of each bacteriophage employed (e.g., in a bacteriophage composition, method or use) will depend upon its virulence against the target bacterial species.

The amount of each bacteriophage employed (e.g. in a bacteriophage composition, method or use as described herein) may depend upon its virulence against the target bacterial isolate.

Pre-selected or baseline bacterial strains may be used in the development of a composition, i.e., bacterial strains which are indicators for individual prospective members of the composition (e.g. panel). A preselected or baseline strain may permit at least 1000 times more plaque formation by one prospective member of the bacteriophage composition than another may. In this way, a composition (e.g. panel) that is consistently effective against a wide range of bacterial isolates may be achieved.

Typically, the one or more bacteriophage(s) may be combined to form a composition including at least about $1\times10^5$, $1\times10^6$, $1\times10^7$, $1\times10^8$, $1\times10^9$ or $1\times10^{10}$, or $1\times10^{11}$ plaque forming units (PFU) of each phage per mL of composition. The composition may include $1\times10^5$ to $1\times10^{11}$ PFU of each phage per mL of composition. In embodiments, the composition may include $1\times10^5$ to $1\times10^6$ PFU, $1\times10^5$ to $1\times10^7$ PFU, $1\times10^5$ to $1\times10^8$ PFU, $1\times10^5$ to $1\times10^9$ PFU, or $1\times10^5$ to $1\times10^{10}$ PFU of each phage per mL of composition. In embodiments, the composition may include $1\times10^6$ to $1\times10^7$ PFU, $1\times10^6$ to $1\times10^8$ PFU, $1\times10^6$ to $1\times10^9$ PFU, $1\times10^6$ to $1\times10^{10}$ PFU, or $1\times10^6$ to $1\times10^{11}$ PFU of each phage per mL of composition. In embodiments, the composition may include $1\times10^7$ to $1\times10^8$ PFU, $1\times10^7$ to $1\times10^9$ PFU, $1\times10^7$ to $1\times10^{10}$ PFU, or $1\times10^7$ to $1\times10^{11}$ PFU of each phage per mL of composition. In embodiments, the composition may include $1\times10^8$ to $1\times10^9$ PFU, $1\times10^8$ to $1\times10^{10}$ PFU, or $1\times10^8$ to $1\times10^{11}$ PFU of each phage per mL of composition. In embodiments, the composition may include $1\times10^9$ to $1\times10^{10}$ PFU or $1\times10^9$ to $1\times10^{11}$ PFU of each phage per mL of composition. In embodiments, the composition may include $1\times10^{10}$ to $1\times10^{11}$ PFU of each phage per mL of composition. In embodiments, one or more bacteriophage(s)

may be combined to form a composition include $1\times10^5$, $1\times10^6$, $1\times10^7$, $1\times10^8$, $1\times10^9$ or $1\times10^{10}$, or $1\times10^{11}$ PFU of each phage per mL of composition. In some embodiments, the composition includes equal (or substantially equal) concentrations of each bacteriophage included herein. Suitable concentrations include any value or subrange within the indicated ranges, including endpoints.

In some aspects, the bacteriophage in the composition are purified or substantially purified.

When selecting bacteriophages for inclusion in a composition of the invention, the methods taught in WO 2013/164640 AI (incorporated herein by reference in its entirety) may be used. In one embodiment, the method comprises: a. providing two or more different bacteriophages, wherein each of the bacteriophages independently retards growth of a target bacteria species or strain; b. combining at least two of the bacteriophages; and c. determining growth of the target bacteria species or strain in the presence of the combination of two or more different bacteriophages, wherein the target bacteria species or strain growth conditions are the same or equivalent in steps a. and c.; d. wherein, if the combination retards growth of the target bacterial species or strain at least equal to the greatest growth retardation achieved independently by any one of the bacteriophages, the combination is accepted as a composition of bacteriophages; and e. wherein, if the combination retards growth of the target bacterial species or strain less than the greatest growth retardation achieved independently by any one of the bacteriophages, the combination is initially rejected as a composition of bacteriophages.

In embodiments, the range of target bacteria affected (i.e. lysed, killed) by the composition is broader than the range of target bacteria affected by any single bacteriophage included within the composition. Such activity may be considered additive and/or synergistic. Activity can be considered synergistic if the effect of the composition (target killing range) is greater than the sum of individual effects (target killing range) of each component bacteriophage.

In one embodiment (alternatively or additionally) a "mutant" bacteriophage is capable of lysing some or all the same target bacterial strains as one or more of *E. coli* phage Ec20, Ec34, Ec35, Ec45, Ec56, and Ec57, and/or further capable of lysing one or more additional bacterial strains. In one embodiment, a mutant may have at least 90%, 91%, 92%, 93%, 94%, 95%, 96%, 97%, 98%, or 99% sequence identity to a nucleic acid sequence of one or more of *E. coli* phage Ec20, Ec34, Ec35, Ec45, Ec56, and Ec57. In some embodiments, a mutant or variant may have at least 90%, 91%, 92%, 93%, 94%, 95%, 96%, 97%, 98%, or 99% sequence identity across its entire genome when compared to one more *E. coli* phage. In one embodiment, a mutant may have at least 93%, 94%, 95%, 96%, 97%, 98%, or 99% sequence identity across its entire genome when compared to SEQ ID NO.: 1, SEQ ID NO.: 2, SEQ ID NO.: 3, SEQ ID NO.: 4, SEQ ID NO.: 5, and/or SEQ ID NO.: 6.

In one embodiment (alternatively or additionally) a "mutant" bacteriophage is capable of lysing some or all the same target bacterial strains as one or more of *B. fragilis* phage Bf1, Bf2, Bf3, and Bf4, and/or further capable of lysing one or more additional bacterial strains. In one embodiment, a mutant may have at least 90%, 91%, 92%, 93%, 94%, 95%, 96%, 97%, 98%, or 99% sequence identity to a nucleic acid sequence of one or more of *B. fragilis* phage Bf1, Bf2, Bf3, and Bf4. In some embodiments, a mutant or variant may have at least 90%, 91%, 92%, 93%, 94%, 95%, 96%, 97%, 98%, or 99% sequence identity across its entire genome when compared to one more of *B. fragilis* phage Bf1, Bf2, Bf3, and Bf4.

In embodiments, a "mutant" may be a bacteriophage progeny. A bacteriophage progeny may be a bacteriophage obtainable after lysing target bacteria (e.g. carcinogenic bacteria) using a bacteriophage as described herein (i.e., the "parent bacteriophage"). In other words, the bacteriophage progeny may be a second (or further) generation bacteriophage.

In embodiments, a bacteriophage progeny is obtainable by contacting one or more bacteriophage(s) described herein, including for example, Ec20, Ec34, Ec35, Ec45, Ec56, Ec57, Bf1, Bf2, Bf3, and/or Bf4, with a target bacteria such that the one or more bacteriophage(s) infects and lyses the target bacteria; and obtaining a bacteriophage released following lysis of the target bacteria. The bacteriophage progeny will typically comprise one or more nucleotide(s) mutation(s) when compared to the relevant parent bacteriophage.

The term "obtainable" as used herein also encompasses the term "obtained." In one embodiment, the term "obtainable" means obtained.

The bacteriophage composition can be an alternative to conventional antibacterial agents and/or cancer therapeutics, and overcomes one or more problems associated therewith. In embodiments, the bacteriophage composition can be utilized as co-treatment or in combination with conventional antibacterial agents and/or cancer therapeutics.

In some embodiments, the composition further comprises an antibiotic (e.g., a chemical antibiotic). In some embodiments, the target bacteria are resistant to one or more antibiotics. In some embodiments, the target bacteria are characterized by the presence of a bacterial biofilm.

In some embodiments, the composition further comprises a cancer therapeutic. In some embodiments, the cancer therapeutic comprises an immunotherapeutic agent. In one embodiment, the immunotherapeutic agent is an immune checkpoint inhibitor. In one embodiment, the immunotherapeutic agent comprises anti-PD-1, anti-PD-L1, anti-CTLA-4, anti-CD27, or anti-IDO-1. In some embodiments, the cancer therapeutic comprises a chemotherapeutic agent. In one embodiment, the chemotherapeutic agent is 5-Fluorouracil (5-FU), capecitabine, irinotecan, oxaliplatin, Trifluridine and/or tipiracil.

In some embodiments, the composition further comprises a pharmaceutically acceptable carrier, diluent, excipient or combinations thereof. In one embodiment, the pharmaceutically acceptable carrier, diluent, excipient or combinations thereof comprises magnesium or calcium salts.

In embodiments, the bacteriophage composition includes a preservative agent for storage. In embodiments, the bacteriophage composition includes a cryoprotectant. In embodiments, the preservative agent is glycerol. In embodiments, the preservative agent and/or cryoprotectant is present in the composition in an amount sufficient to preserve the composition, for example during storage in a freezer or ultra-freezer (e.g., at temperatures from about 0° C. to about −80° C., more preferably from about −20° C. to about −80° C., most preferably about −80° C.), or in liquid nitrogen. In a more preferred embodiment, the preservative agent is present in the composition in an amount sufficient to preserve the composition during long-term storage, e.g., in a freezer, ultra-freezer, or liquid nitrogen. In one embodiment, the preservative agent is between about 5% and about 50% glycerol; more preferably between about 10% and about 30% glycerol; most preferably about 20% glycerol. Suitable concentrations may be any value or sub value within the recited ranges, including endpoints.

In embodiments, the composition is an oral freeze-dried, spray freeze-dried, aerosolized formulation of the composition. In some embodiments, the composition is administered intravenously. In some embodiments, the composition is administered orally with and without micro-encapsulated or nano delivery systems. In some embodiments, the composition is administered as a suppository.

Formulations

Provided herein are bacteriophage compositions that include or consist essentially of one more of the bacteriophages described herein. In some aspects the compositions can be substantially free of bacterial components, such as for example, bacterial endotoxin, bacterial host cell components and materials (e.g., protein), and the like. In some embodiments, the compositions includes one or more obligately lytic bacteriophages. The one or more bacteriophages may include a nucleic acid, for example, a genome including a nucleotide sequence having 85%-100% identity to one or more of SEQ ID NOs: 1-6. In some embodiments, at least one or more phages have at least 85%, but not 100%, nucleic acid sequence identity to any one of SEQ ID NOs: 1-6. Each individual bacteriophage may be one that is not prone to generalized transduction and/or does not carry antibiotic resistance genes. The phage can be naturally occurring or non-naturally occurring. In some embodiments for example, in compositions with more than one bacteriophage, at least one can be naturally occurring, at least one can be non-naturally occurring, or none can be naturally occurring. The compositions optionally may include a cryoprotectant or excipient. The excipient may stabilize phage potency or reduce potency loss over time, for example.

In some embodiments, bacteriophage compositions provided herein further include a pharmaceutically acceptable carrier, diluent, excipient or combinations thereof. Suitable carriers, diluents and/or excipients may include isotonic saline solutions, such as phosphate-buffered saline. "Pharmaceutically acceptable excipient" and "pharmaceutically acceptable carrier" refer to a substance that aids the administration of an active agent to and/or absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, lactose, leucine, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts e.g. for influencing osmotic pressure, buffers, coloring, and/or aromatic substances and the like that do not deleteriously react with the compounds of the disclosure. One of skill in the art will recognize that other pharmaceutical excipients are useful in the present disclosure.

A bacteriophage composition as described herein may be formulated for nasal, oral, parenteral, intramuscular, intravenous, or subcutaneous administration. Such a bacteriophage preparation may be used directly, refrigerated, lyophilized, stored frozen in aqueous or other solution, optionally with an appropriate cryoprotectant (e.g. 20% glycerol), freeze dried and rehydrated prior to use, or rendered stable in some other formulation including (but not limited to) tablet, emulsion, ointment, or impregnated wound dressing or other item. In embodiments, the cyroprotectant is 10-30% glycerol. In embodiments, the cryoprotectant is 10%, 11%, 12%, 13%, 14%, 15%, 16%, 17%, 18%, 19% 20%, 21%, 22%, 23%, 24%, 25%, 26%, 27%, 28%, 29%, or 30% glycerol.

In embodiments, the bacteriophage composition includes saline (e.g., phosphate buffered saline, with or without magnesium). In embodiments, the bacteriophage composition includes a buffer. In embodiments, the buffer includes calcium or magnesium salts. In an embodiment, the buffer includes phosphate buffered saline and $MgSO_4$. The buffer may include 1 mM to 20 mM $MgSO_4$, 2 mM to 19 mM $MgSO_4$, 3 mM to 17 mM $MgSO_4$, 4 mM to 16 mM $MgSO_4$, 5 mM to 15 mM $MgSO_4$, 6 mM to 14 mM $MgSO_4$, 7 mM to 13 mM $MgSO_4$, 8 mM to 12 mM $MgSO_4$, 9 mM to 11 mM $MgSO_4$, or about 10 mM $MgSO_4$. The concentration may be any value or subrange within the recited ranges, including endpoints. For example, the buffer may include about 1 mM $MgSO_4$, about 2 mM $MgSO_4$, about 3 mM $MgSO_4$, about 4 mM $MgSO_4$, about 5 mM $MgSO_4$, about 6 mM $MgSO_4$, about 7 mM $MgSO_4$, about 8 mM $MgSO_4$, about 9 mM $MgSO_4$, about 10 mM $MgSO_4$, about 11 mM $MgSO_4$, about 12 mM $MgSO_4$, about 13 mM $MgSO_4$, about 14 mM $MgSO_4$, about 15 mM $MgSO_4$, about 16 mM $MgSO_4$, about 17 mM $MgSO_4$, about 18 mM $MgSO_4$, about 19 mM $MgSO_4$, or about 20 mM $MgSO_4$. In embodiments, the buffer includes calcium chloride, $CaCl_2$). The buffer may include 1 mg/L to 20 mg/L $CaCl_2$), 2 mg/L to 19 mg/L $CaCl_2$), 3 mg/L to 17 mg/L $CaCl_2$), 4 mg/L to 16 mg/L $CaCl_2$), 5 mg/L to 15 mg/L $CaCl_2$), 6 mg/L to 14 mg/L $CaCl_2$), 7 mg/L to 13 mg/L $CaCl_2$), 8 mg/L to 12 mg/L $CaCl_2$), 9 mg/L to 11 mg/L $CaCl_2$, or about 10 mg/L $CaCl_2$). For example, the buffer may include about 1 mg/L $CaCl_2$), about 2 mg/L $CaCl_2$), about 3 mg/L $CaCl_2$), about 4 mg/L $CaCl_2$), about 5 mg/L $CaCl_2$), about 6 mg/L $CaCl_2$), about 7 mg/L $CaCl_2$), about 8 mg/L $CaCl_2$), about 9 mg/L $CaCl_2$), about 10 mg/L $CaCl_2$), about 11 mg/L $CaCl_2$), about 12 mg/L $CaCl_2$), about 13 mg/L $CaCl_2$), about 14 mg/L $CaCl_2$), about 15 mg/L $CaCl_2$), about 16 mg/L $CaCl_2$), about 17 mg/L $CaCl_2$), about 18 mg/L $CaCl_2$), about 19 mg/L $CaCl_2$), or about 20 mg/L $CaCl_2$).

A bacteriophage composition may be formulated for nasal, oral, parenteral, intramuscular, intravenous, or subcutaneous administration. Such a bacteriophage preparation may be used directly, stored frozen in aqueous or other solution, optionally with an appropriate cryoprotectant (e.g., 10% sucrose or glycerol), stored in refrigeration temperatures, freeze dried and rehydrated prior to use, or rendered stable in some other formulation including (but not limited to) tablet, emulsion, ointment, or impregnated wound dressing or other item. In some embodiments, the bacteriophage composition may be comprised in an intravenous delivery means.

In some embodiments, the bacteriophage composition is sterile. Such a sterile product may be suitable for parenteral administration in a subject.

In some embodiments, provided herein are oral formulations including the bacteriophage and/or bacteriophage compositions/formulations as described herein. Some embodiments relate to methods and uses of such oral formulations.

Uses/Methods of Use

Provided herein is a use of one or more bacteriophage or a bacteriophage composition as a medicament (e.g., for treating or preventing cancer). Corresponding methods of treating a disease comprising administration of the one or more bacteriophage or bacteriophage composition(s) to a subject are also provided.

In an aspect, there is provided a bacteriophage composition for use in treating a bacterial infection. In related aspects, there is provided use of a bacteriophage composition in the manufacture of a medicament for treating a bacterial infection, as well as a method of treating a bacterial infection comprising administering the bacteriophage composition to a subject.

In an aspect, provided herein are methods of treating a bacterial-associated cancer including selecting a subject with a confirmed infection of a bacteria associated with cancer and administering a bacteriophage composition as described herein. In one embodiment, the method comprises selecting a subject with an infection of a bacteria associated with cancer. In embodiments, the method includes selecting a patient having colorectal cancer. In embodiments, the method includes selecting a patient having a pks+*E. coli* infection. In embodiments, the method includes selecting a patient having a pks+*E. coli* infection. In embodiments, the method includes selecting a patient having a pks+*E. coli* strain infection. In embodiments, the method includes selecting a patient having colorectal cancer due to infection by *E. coli* bacteria. In embodiments, the method includes selecting a patient having a *Bacteroides fragilis* infection. In embodiments, the method includes selecting a patient having a *B. fragilis* Clindamycin resistant infection. In embodiments, the method includes selecting a patient having a *B. fragilis* Clindamycin sensitive infection. In embodiments, the method includes selecting a patient having colorectal cancer due to infection by *B. fragilis* bacteria.

In embodiments, the subject has a genetic predisposition for one or more additional cancers. In some embodiments, the subject has been screened for a genetic mutation that predisposes the patient to cancer. In some embodiments, the genetic mutation is familial adenomatous polyposis.

The cancer may be any cancer that is known or suspected of being due to infection by a bacterial species or strain. Cancers or tumors that can be treated by the compositions and methods described herein include, but are not limited to: biliary tract cancer; brain cancer, including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyo sarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma [teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors include breast cancer, lymphoma, multiple myeloma, and melanoma. In embodiments, the cancer is colorectal cancer, esophageal cancer, gallbladder cancer, lung cancer, squamous cell carcinoma, bladder cancer, stomach cancer, or MALT lymphoma. In embodiments, the cancer is colorectal cancer. In embodiments, the cancer is esophageal cancer. In embodiments, the cancer is gallbladder cancer. In embodiments, the cancer is lung cancer. In embodiments, the cancer is squamous cell carcinoma. In embodiments, the cancer is bladder cancer. In embodiments, the cancer is stomach cancer. In embodiments, the cancer is MALT lymphoma.

In some embodiments, the infection is characterized by the presence of a bacterial biofilm. In some embodiments, the bacterial infection is chronic. In some embodiments, the bacterial infection is acute.

In some embodiments, the subject has a bacterial infection that is not responding to one or more antibiotics. In some embodiments, the subject has a bacterial infection that is not responding to standard-of-care antibiotics.

In embodiments, one or more bacterial isolates from the subject is tested for susceptibility to the bacterial composition prior to administration.

As used herein, a "therapeutically effective amount" is any amount of the composition, which when administered alone or in combination to a subject for treating a bacterial infection (or a symptom thereof) is sufficient to effect such treatment of the infection, or symptom thereof.

As used herein, a "prophylactically effective amount" is any amount of the composition that, when administered alone or in combination to a subject inhibits or delays the onset or reoccurrence of a bacterial infection (or a symptom thereof). In some embodiments, the prophylactically effective amount prevents the onset or reoccurrence of a bacterial infection entirely. "Inhibiting" the onset means either lessening the likelihood of a bacterial infection's onset (or symptom thereof), or preventing the onset entirely.

An appropriate dosage range is one that produces the desired therapeutic effect (e.g., the composition is dosed in a therapeutically or prophylactically effective amount).

In one embodiment, the subject is a human subject with a bacterial associated cancer (e.g. colorectal cancer). In embodiments, the composition includes $1 \times 10^5$ to $1 \times 10^{11}$ PFU of each phage per mL of composition. In embodiments, the composition includes $1 \times 10^5$ to $1 \times 10^6$ PFU, $1 \times 10^5$ to $1 \times 10^7$ PFU, $1 \times 10^5$ to $1 \times 10^8$ PFU, $1 \times 10^5$ to $1 \times 10^9$ PFU, or $1 \times 10^5$ to $1 \times 10^{10}$ PFU of each phage per mL of composition. In embodiments, the composition includes $1 \times 10^5$ to $1 \times 10^7$ PFU, $1 \times 10^6$ to $1 \times 10^8$ PFU, $1 \times 10^6$ to $1 \times 10^9$ PFU, $1 \times 10^6$ to $1 \times 10^{10}$ PFU, or $1 \times 10^6$ to $1 \times 10^{11}$ PFU of each phage per mL of composition. In embodiments, the composition includes $1 \times 10^7$ to $1 \times 10^8$ PFU, $1 \times 10^7$ to $1 \times 10^9$ PFU, $1 \times 10^7$ to $1 \times 10^{10}$ PFU, or $1 \times 10^7$ to $1 \times 10^{11}$ PFU of each phage per mL of composition. In embodiments, the composition includes $1 \times 10^8$ to $1 \times 10^9$ PFU, $1 \times 10^8$ to $1 \times 10^{10}$ PFU, or $1 \times 10^8$ to $1 \times 10^{11}$ PFU of each phage per mL of composition. In embodiments, the composition includes $1 \times 10^9$ to $1 \times 10^{10}$ PFU or $1 \times 10^9$ to $1 \times 10^{11}$ PFU of each phage per mL of composition. In embodiments, the composition may include $1 \times 10^{10}$ to $1 \times 10^{11}$ PFU of each phage per mL of composition.

In embodiments, a bacteriophage composition is administered to a subject at a dosage of at least about $1 \times 10^5$ PFU of each phage, at least about $1 \times 10^6$ PFU of each phage, at least about $1 \times 10^7$ PFU of each phage, at least about $1 \times 10^8$ PFU of each phage, at least about $1 \times 10^9$ PFU of each phage, at least about $1 \times 10^{10}$ PFU of each phage, or at least about $1 \times 10^{11}$ PFU of each phage per mL of composition. In embodiments, one or more bacteriophage(s) may be combined to form a composition including $1 \times 10^5$, $1 \times 10^6$, $1 \times 10^7$, $1 \times 10^8$, $1 \times 10^9$, or $1 \times 10^{10}$ or $1 \times 10^{11}$ PFU of each phage per mL of composition. Dosages include any value or range within the recited ranges, including endpoints.

In some embodiments, bacteriophage compositions provided herein are administered to a subject at a dosage of at least about $1\times10^5$ PFU total phage, at least about $1\times10^6$ PFU total phage, at least about $1\times10^7$ PFU total phage, at least about $1\times10^8$ PFU total phage, at least about $1\times10^9$ PFU total phage, at least about $1\times10^{10}$ PFU total phage, or at least about $1\times10^{11}$ PFU of total phage. The bacteriophage composition is administered at a dosage of between about $1\times10^5$ to about $1\times10^{11}$ PFU of total phage per mL of composition. In embodiments, the bacteriophage composition is administered at a dosage of between about $1\times10^5$ to about $1\times10^6$ PFU, between about $1\times10^5$ to about $1\times10^7$ PFU, between about $1\times10^5$ to about $1\times10^8$ PFU, between about $1\times10^5$ to about $1\times10^9$ PFU, or between about $1\times10^5$ to about $1\times10^{10}$ PFU of total phage per mL of composition. In embodiments, the bacteriophage composition is administered at a dosage of between about $1\times10^6$ to about $1\times10^7$ PFU, between about $1\times10^6$ to about $1\times10^8$ PFU, between about $1\times10^6$ to about $1\times10^9$ PFU, between about $1\times10^6$ to about $1\times10^{10}$ PFU, or between about $1\times10^6$ to about $1\times10^{11}$ PFU of total phage per mL of composition. In embodiments, the bacteriophage composition is administered at a dosage of between about $1\times10^7$ to about $1\times10^8$ PFU, between about $1\times10^7$ to about $1\times10^9$ PFU, between about $1\times10^7$ to about $1\times10^{10}$ PFU, or between about $1\times10^7$ to about $1\times10^{11}$ PFU of each phage per mL of composition. In embodiments, the bacteriophage composition is administered at a dosage of between about $1\times10^8$ to about $1\times10^9$ PFU, between about $1\times10^8$ to about $1\times10^{10}$ PFU, or between about $1\times10^8$ to about $1\times10^{11}$ PFU of total phage per mL of composition. In embodiments, the bacteriophage composition is administered at a dosage of between about between about $1\times10^9$ to about $1\times10^{10}$ PFU, or between about $1\times10^9$ to about $1\times10^{11}$ PFU of total phage per mL of composition. In embodiments, the bacteriophage composition is administered at a dosage of between about $1\times10^{10}$ to about $1\times10^{11}$ PFU of total phage per mL of composition. A dosage may be $3\times10^9$ PFU per milliliter composition. Dosages include any value or range within the recited ranges, including endpoints.

In some embodiments, the bacteriophage composition is administered at least once, twice, three times, or four times daily. Suitably the bacteriophage composition may be administered twice daily. In one embodiment, therefore, a dosage of at least about $1\times10^5$ PFU of each phage is administered at least once, twice, three times, or four times daily. In one embodiment, therefore, a dosage of at least about $1\times10^6$ PFU of each phage is administered at least once, twice, three times, or four times daily. In another embodiment at least about $1\times10^7$ PFU of each phage is administered at least once, twice, three times, or four times daily. In a further embodiment at least about $1\times10^8$ PFU of each phage is administered at least once, twice, three times, or four times daily. In another embodiment at least about $1\times10^9$ PFU of each phage is administered at least once, twice, three times, or four times daily. In another embodiment at least about $1\times10^{10}$ PFU of each phage is administered at least once, twice, three times, or four times daily. In another embodiment at least about $1\times10^{11}$ PFU of each phage is administered at least once, twice, three times, or four times daily. A dosage range between about $1\times10^5$ PFU of each phage to about $1\times10^{11}$ PFU of each phage may be administered at least once, twice, three times, or four times daily. Preferably a dosage range between about $1\times10^7$ PFU of each phage to about $1\times10^9$ PFU of each phage may be administered at least once, twice, three times, or four times daily.

In some embodiments, the bacteriophage composition is administered every 2 hours, every 4 hours, every 6 hours, every 8 hours, every 12 hours, every 24 hours, every 48 hours, or every 72 hours. In some embodiments, the bacteriophage composition is administered every 2 hours. In some embodiments, the bacteriophage composition is administered every 4 hours. In some embodiments, the bacteriophage composition is administered every 6 hours. In some embodiments, the bacteriophage composition is administered every 8 hours. In some embodiments, the bacteriophage composition is administered every 12 hours. In some embodiments, the bacteriophage composition is administered every 24 hours. In some embodiments, the bacteriophage composition is administered every 48 hours. In some embodiments, the bacteriophage composition is administered every 72 hours. Frequency of administration include any value or range within the recited ranges, including endpoints.

In some embodiments, the bacteriophage composition is administered for at least one day, at least 2 days, at least 3 days, at least 4 days, at least 5 days, at least 6 days, one week, at least two weeks, at least three weeks, at least four weeks, at least 5 weeks, at least 6 weeks, at least 7 weeks, at least 8 weeks, at least 9 weeks, at least 10 weeks, or more than 10 weeks. In some embodiments, the bacteriophage composition is administered for at least one day. In some embodiments, the bacteriophage composition is administered for at least one week. In some embodiments, the bacteriophage composition is administered for at least two weeks. In some embodiments, the bacteriophage composition is administered for at least three weeks. In some embodiments, the bacteriophage composition is administered for at least four weeks. In some embodiments, the bacteriophage composition is administered for at least five weeks. In some embodiments, the bacteriophage composition is administered for at least six weeks. In some embodiments, the bacteriophage composition is administered for between about 3 days and about 100 days. In an embodiment, the bacteriophage composition is administered for between about 7 days and about 60 days. In an embodiment, the bacteriophage composition is administered for between about 14 days and about 30 days. In an embodiment, the bacteriophage composition is administered for between about 3 days and about 28 days. In an embodiment, the bacteriophage composition is administered for at least 14 days. In an embodiment, the bacteriophage composition is administered for greater than 14 days. Duration of administration includes any value or range within the recited ranges, including endpoints. In embodiments, treatment may be delivered prophylactically (i.e. if the bacteria is detected, there is a genetic predisposition to cancer, but no cancer detected yet) to decontaminate the gut. In those instances, decolonization periods could be as long as those of treatment as described above.

A bacteriophage composition for use as a medicament may be administered by any route selected based on the condition to be treated. In one embodiment the route of administration is nasal, oral, pulmonary, parenteral, intramuscular, intravenous, subcutaneous, transdermal, ocular, aural or combinations thereof. In embodiments, the route of administration is oral. The composition may be administered to the patient via more than one route, for example oral and intravenous.

In one embodiment an antibiotic (suitably a chemical antibiotic) may be administered in combination with the bacteriophage composition of the invention. Combinatorial administration of antibiotics and bacteriophages is taught in WO 2008/110840 and WO 2005/009451, which teaching is incorporated herein by reference in its entirety. The antibiotic may be administered simultaneously or sequentially with the bacteriophage composition. Suitably, the one or more antibiotics may be administered after the composition such that bacteriophage replication has become established before antibiotic treatment begins. In this case, antibiotic treatment may be delayed for one or more hours or days from application of the one or more bacteriophages, e.g., from 1 to 2, 3, 4, 5, 6, 7, 8, 9 or 10 days. Where a bacteriophage composition comprising a plurality of bacteriophages is employed with each member of the composition exhibiting different strain specificity, it will suffice that at least a proportion (e.g., one or more bacteriophage(s)) of the composition is capable of targeting the bacterial infection.

Thus, in some embodiments a bacteriophage composition comprises one or more antibiotics, such as one or more chemical antibiotics. An antibiotic may be selected based on sensitivity of the target species or strain to said antibiotic. Suitably the species or strain may be the same species or strain present in a subject to be treated. In one embodiment, a species or strain is taken from a subject to be treated and tested for antibiotic sensitivity. Sensitivity may be determined by in vitro sensitivity assays known in the art.

Alternatively or additionally, an antibiotic may be selected because it is known to be active against a bacteria known to be (or thought likely to be) present together with a bacterial infection to be treated (e.g., as part of a bacterial biofilm).

In one embodiment and without limitation, an antibiotic is one or more selected from: a penicillin, a lincosamide, a monobactam, a cephalexin, a macrolide, a fluoroquinolone, a sulfonamide, a tetracycline, a cephalosporin, a cephamycin, a carbapenem a glycylcycline, a phenicol, a folate pathway inhibitor, a polymyxin, a phosphonic acid, a nitroimidazole, or an aminoglycoside.

In one embodiment, a use or method of the invention comprises: a. administration of a bacteriophage composition to a subject in vivo; b. in vitro monitoring of the sensitivity of a sample of bacterial cells from an infection (e.g., present in the subject) or from another infection by the same strain to one or more antibiotic(s); and c. administration of said one or more antibiotic(s), when it has been established that said sensitivity to said one or more antibiotic(s) has been induced.

In one embodiment, the antibiotic (e.g., chemical antibiotic) is administered at a time period at which sensitivity of sampled bacteria to the antibiotic is induced by the composition. In some embodiments, the time period may be at least 12, 24 or 48 hours. In other embodiments, the bacteriophage composition and the antibiotic may be administered at intervals of one day to two months apart, preferably at intervals of one to four weeks apart, suitably at intervals of two weeks apart.

In embodiments, provided herein are methods for restoring sensitivity to an antibiotic(s) by administering a composition as described herein. In embodiments, provided herein methods for disrupting a biofilm by administering a composition as described herein. In embodiments, provided herein are methods for destroying a biofilm by administering a composition as described herein.

In some embodiments, the bacteriophage composition as described herein may be administered with at least one additional cancer treatment. In one embodiment, the at least one additional cancer treatment comprises an immunotherapeutic agent. Immunotherapeutic agents include, for example and without limitation, checkpoint inhibitors, anti-tumor antibodies (therapeutic antibodies), cancer vaccines, and other cancer treatments that boost the immune system. In one embodiment, the immunotherapy agent comprises anti-PD-1, anti-PD-L1, anti-CTLA-4, anti-CD27, or anti-IDO-1. Examples of PD-1 inhibitors include, without limitation, pembrolizumab, nivolumab, pidilizumab, AMP-224, AMP-514, and PDR001. Examples of PD-L1 inhibitors include, without limitation, atezolizumab, avelumab, durvalumab, and BMS-936559.

In some embodiments, the one or more additional agents comprise a chemotherapeutic agent. In one embodiment, the chemotherapeutic agent is 5-Fluorouracil (5-FU), capecitabine, irinotecan, oxaliplatin, Trifluridine and/or tipiracil. Additional anti-cancer agents, including additional immunotherapy and chemotherapy agents, are well known in the art.

The type and dose of the anti-cancer agent can be determined by a skilled clinician. For example and without limitation, anti-cancer agents approved for stomach (gastric) cancers include Cyramza (Ramucirumab), Docetaxel, Doxorubicin Hydrochloride, 5-FU (Fluorouracil Injection), Fluorouracil Injection, Herceptin (Trastuzumab), Mitomycin C, Mitozytrex (Mitomycin C), Mutamycin (Mitomycin C), Ramucirumab, Taxotere (Docetaxel), Trastuzumab, FU-LV, TPF, XELIRI. Anti-cancer agents approved for colon and/or rectal cancer include, for example and without limitation, Avastin (Bevacizumab), Camptosar (Irinotecan Hydrochloride), Capecitabine, Cetuximab, Cyramza (Ramucirumab), Eloxatin (Oxaliplatin), Erbitux (Cetuximab), 5-FU (Fluorouracil Injection), Fluorouracil Injection, Irinotecan Hydrochloride, Leucovorin Calcium, Lonsurf (Trifluridine and Tipiracil Hydrochloride), Nivolumab, Opdivo (Nivolumab), Oxaliplatin, Panitumumab, Ramucirumab, Regorafenib, Stivarga (Regorafenib), Trifluridine and Tipiracil Hydrochloride, Vectibix (Panitumumab), Wellcovorin (Leucovorin Calcium), Xeloda (Capecitabine), Zaltrap (Ziv-Aflibercept), Ziv-Aflibercept, CAPDX, FOLFIRI, FOLFIRI-BEVACIZUMAB, FOLFIRI-CETUXIMAB, FOLFOX, FU-LV, XELIRI, and XELOX.

The present invention also provides a kit comprising: a bacteriophage composition according to the invention; and instructions for use of same (e.g., in medicine). The kit may further comprise an additional agent, such as an antibiotic (e.g., a chemical antibiotic), an immunotherapeutic agent, or a chemotherapeutic agent, and optionally instructions for use of same in combination with the bacteriophage composition.

In one embodiment, the instructions provide details for dosing a bacteriophage composition of the invention as described herein.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the example methods and materials disclosed herein, and any methods and materials similar or equivalent to those described herein can be used in the practice or testing of embodiments of this disclosure. Numeric ranges are inclusive of the numbers defining the range. The headings provided herein are not limitations of the various aspects or embodiments of this disclosure which can be had by reference to the specification as a whole.

Before the example embodiments are described in more detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

The publications discussed herein are provided solely for their disclosure prior to the filing date of the present application. Nothing herein is to be construed as an admission that such publications constitute prior art to the claims appended hereto. All publications referenced herein are incorporated herein by reference in their entireties.

The invention will now be described, by way of example only, with reference to the following Figures and Examples.

EXAMPLES

Example 1 Assembly of Bacteriophage Cocktail

A cocktail of two to four bacteriophages, which together have broad activity against a panel of recent diverse *E. coli* clinical isolates, is used in animal studies. In an example method, phage lysates are prepared using one or more manufacturing hosts (e.g., *E. coli* strains numbers SPS69, SPS759, SPS765, SPS932), preferably which do not release endogenous prophage(s) during the production cycle. Cultures are grown in bioreactors to an $OD_{600}$ 0.2 prior to phage addition. Incubation at 37° C. is continued and absorbance read at least every 60 minutes. Cultures are harvested after bacterial lysis, and impurities separated from the phages with several filtration steps followed by chromatographic steps that enable reduction of debris such as host cell proteins and host cell DNA, such that final phage titers are $\geq 1 \times 10^{11}$ PFU/mL. At the end of the process, buffer is exchanged and all material is filter-sterilized (0.22 pm filter) and stored at 2-8° C. Plaque assays can be used to titer the phage stocks (Carlson, K., In E. Kutter and A. Sulakvelidze (ed.), Bacteriophages: Biology and Application, (2005) 437-494, CRC Press, Boca Raton, FL, Hyman, P., et al., *Meth. Mol. Biol.* (2009) 501:175-202). The purified phage samples are diluted 1:10, 1:100 or 1:1000 to obtain the dosing solutions and subsequently combined such that each phage is present in the final cocktail at the desired concentration (e.g., about $2 \times 10^{10}$ $2 \times 10^9$ or $2 \times 10^8$ PFU/mL) per phage. Final endotoxin levels are determined.

Example 2 Phage Isolation and Characterization

The following experiments were conducted in an effort to assess in preclinical models the potential of bacteriophages as targeted therapeutics for *E. coli* and *B. fragilis* driven cancers.

Relevant bacteria strains were provided by Johns Hopkins University. Three strains of bacteria were received: 1. *Bacteroides fragilis* 086 (Clindamycin resistant)—AmpliPhi ID #2849; 2. *Bacteroides fragilis* NCTC 9343 (Clindamycin sensitive)—AmpliPhi ID #2850; 3. *E. coli* PL1 (pks+*E. coli*)—AmpliPhi ID #2851.

*Bacteroides* Phage Isolation and Characterization

The *Bacteroides fragilis* strains were grown anaerobically on BHI/Yeast Extract/L-Cysteine agar plates supplemented with Hemin and Vitamin K1 as requested by JHU and stocks prepared on both beads and in 30% glycerol/BHI broth. Stocks were stored frozen at −80° C.

Phage isolation was undertaken for the *Bacteroides fragilis* isolates. Using sewage water samples from the Sydney (Australia) area, phages were successfully isolated against *B. fragilis* ID #2849. Plaque purification of four selected phages (preliminary chosen based on their differing plaque morphology and origin of sewage water samples) was performed and master stocks prepared in phage buffer. Master research stocks of the *Bacteroides fragilis* phages Bf1, Bf2, Bf3 and Bf4, targeting *Bacteroides fragilis* 086 (ID #2849), were propagated by the plate method and further characterized as described in Table 1.

Plate Method: BHI/Yeast Extract/L-Cysteine agar plates supplemented with Hemin and Vitamin K1 were used to propagate the phages. A bacteriophage dilution that was likely to give plates with "confluent lysis" was prepared and mixed with an aliquot of an overnight BHI/Yeast Extract/L-Cysteine supplemented with Hemin and Vitamin K1 broth culture of *Bacteroides fragilis* 086 (ID #2849). 3 mL of BHI/Yeast Extract/L-Cysteine semi-solid supplemented with Hemin and Vitamin K1 agar tempered to 47.5° C. (+/−2.5) in a waterbath was applied to the surface of BHI/Yeast Extract/L-Cysteine agar plates. The plates were incubated under anaerobic conditions at 37° C. overnight. Salt-Magnesium (SM) buffer was added to the plates at 4° C. overnight to elute the bacteriophages. The eluted phages were then filtered through 0.22 μm PES filter and stored at 4° C.

TABLE 1

Characteristics of *Bacteroides fragilis* phages

| AmpliPhi Phage ID# | AmpliPhi Host Strain ID# | Plaque Diameter & Description | Estimated Genome Molecular Weight (kb) | Master stock Titre (PFU/mL) |
|---|---|---|---|---|
| Bf1 | 2849 | 1.5 mm, clear | 43 | $1.1 \times 10^{10}$ |
| Bf2 | 2849 | 2 mm, clear, tiny halo | 45 | $1.3 \times 10^{11}$ |
| Bf3 | 2849 | <1 mm, clear | 46 | $6.0 \times 10^{10}$ |
| Bf4 | 2849 | 1 mm, clear | 46.5 | $3.0 \times 10^{10}$ |

The activity of phages Bf1, Bf2, Bf3 and Bf4 against Clindamysin sensitive *Bacteroides fragilis* (ID #2850) was performed by the spot test method.

Method: Phage activity was assessed by the spot test method, (a modification of the small drop agar overlay method (Mazzocco, 2009)). Briefly, planktonic bacterial culture was mixed with molten dilute agar and poured evenly over an agar plate. When the top agar layer was set, serial dilutions of standardized phage solutions were spotted onto the overlay and plates incubated overnight at 37° C. Phage activity was indicated by clearing of the bacterial lawn at the site of phage application, and by the development of individual plaques as the phage sample is diluted. Strains were only considered sensitive if discrete plaques could be observed as the sample was diluted, indicating phage replication in addition to cell death.

Results are presented in Table 2. Two of the phages, Bf1 and Bf3, that had been isolated against *B. fragilis* ID #2849 were also active against *B. fragilis* ID #2850

TABLE 2

Host Range activity of *B fragilis* phages

|  | Bf1 | Bf2 | Bf3 | Bf4 |
|---|---|---|---|---|
| Bacterial Strain ID # 2849 Clindamycin Resistant | 1.10E+10 | 1.30E+11 | 6.00E+10 | 3.00E+10 |
| Bacterial Strain ID # 2850 Clindamycin Sensitive | 1.00E+05 | 0 | 1.35E+08 | 0 |

Confirmation of In Vitro Activity in Broth Culture

The activity of the four *B. fragilis* phages was also evaluated in vitro in liquid culture in an attempt to understand the phage infection process over time.

Method: 96 well culture plates were prepared with each test well containing 200 μl of a 1/100 overnight culture of *B. fragilis* ID #2849 or *B. fragilis* ID #2850 in BHI/Yeast Extract/L-Cysteine supplemented with Hemin and Vitamin K1 broth. 20 μl of phages Bf1-Bf4 and 20 μl of the phage mix (all 4 phages) were added to the appropriate wells and control wells containing only bacteria were included. The plates were incubated anaerobically for 21 hrs. OD readings at 500-700 nm (Cell growth program) were taken in the Spectrostar plate reader at Time=0 and again at T=6 hours and T=21 hours.

The results obtained in broth culture for *B. fragilis* ID #2849 reflect those seen in the spot test with each phage and the mix inhibiting the growth of the bacteria. (FIG. 1).

Figure 2:
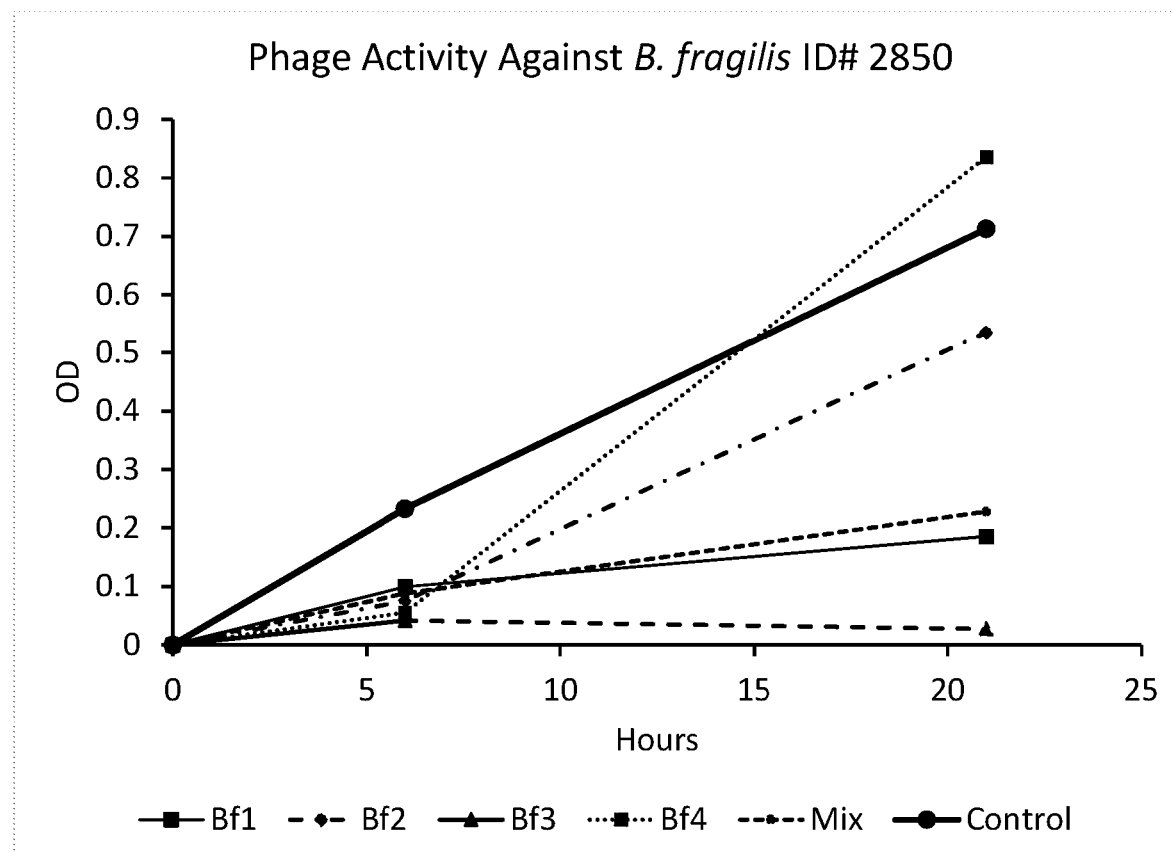
FIG. 2 is a graph of phage activity of four different phage and a mixture of phage against a *Bacteroides fragilis* strain (Clindamycin sensitive).
Figure 3:
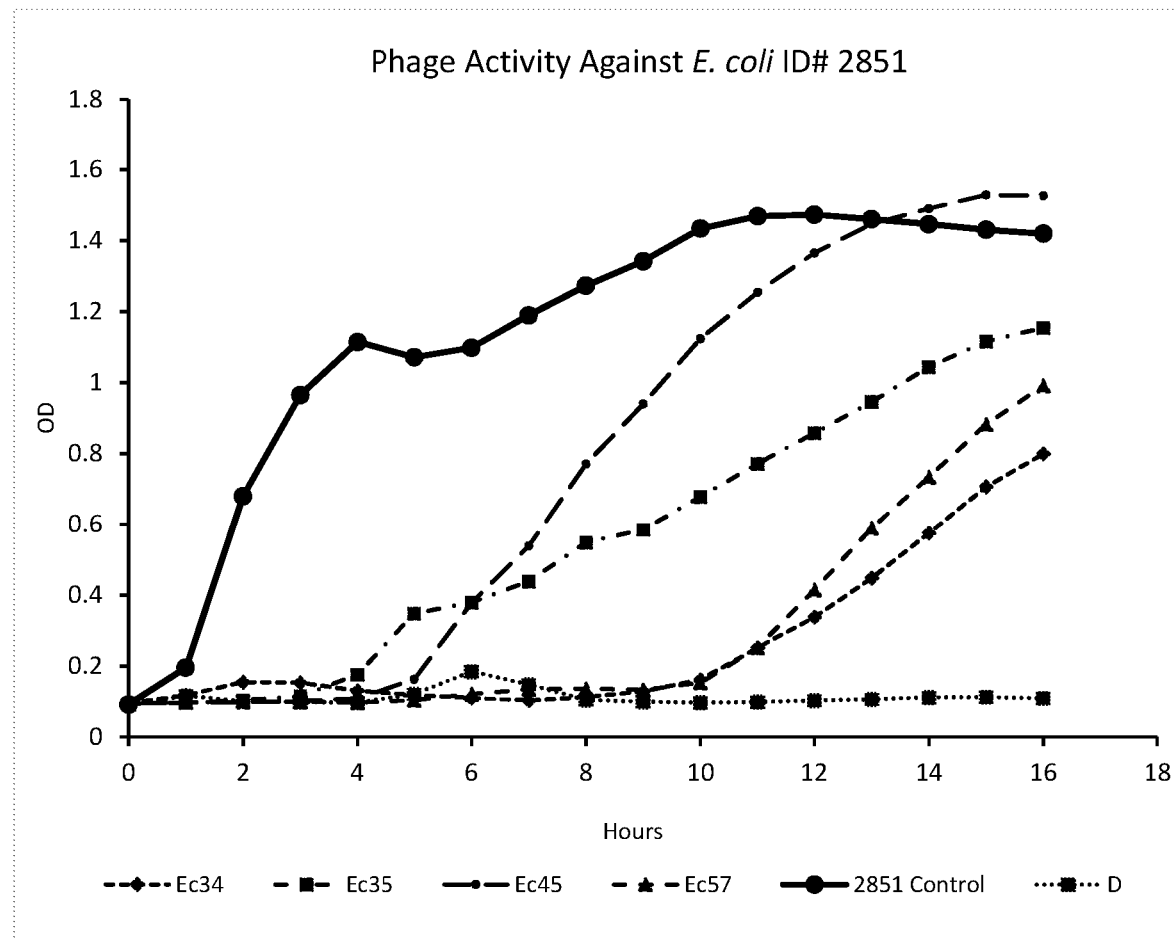
FIG. 3 is a graph of phage activity of four different phage and a mixture of phage against an *Escherichia coli* strain (pks+).

In the spot test, only Bf1 and Bf3 demonstrated active growth against *B. fragilis* ID #2850. The results in broth culture showed that Bf1, Bf3 and the phage mix prevent the growth of the bacteria reflecting the results seen on solid media in the spot test (FIG. 2).

pH Stability Testing of *B. fragilis* Phages

The stability at low pH of the four phages was tested in order to determine their suitability for gavage administration in the mouse model and potential oral delivery in the clinic.

Method: Each of the four phages were diluted in SM buffer pH 7.5 to give an approximately starting concentration of $10^9$ PFU/mL. The phages were then diluted 1/10 from this starting material in SM buffer pH 7.5 (neutral) and SM buffer pH 3.0 (low). Following incubation at 37° C. for 1 hour the samples were serially diluted in SB buffer (pH 7.5) to evaluate the titer by the spot test as described above. Results are shown in Table 3.

TABLE 3 pH stability results

|  | Titre (PFU/mL) pH 7.5 | Titre (PFU/mL) pH 3.0 |
|---|---|---|
| Bf1 | $1.1 \times 10^7$ | $8.0 \times 10^6$ |
| Bf2 | $1.2 \times 10^8$ | $8.0 \times 10^7$ |
| Bf3 | $6.0 \times 10^7$ | $4.4 \times 10^7$ |
| Bf4 | $1.8 \times 10^7$ | $9.0 \times 10^6$ |

The *Bacteroides* phages Bf1, Bf2, Bf3 and Bf4 are resistant to low pH 3.0 at 37° C. for 1 hour making them good candidates for oral delivery.

Example 3. *E. coli* Phage Isolation and Characterization

A pks+*E. coli* strain was grown on nutrient agar and stocks prepared on both beads and in 30% glycerol/nutrient broth. Stocks were stored frozen at −80° C.

The target *E. coli* strain (pks+*E. coli*) AmpliPhi ID #2851 was spot tested (as described above) with four *E. coli* phages (Ec34, Ec35, Ec45, and Ec57) that had been short listed and identified as potential therapeutic components in an *E. coli* investigational product.

All of these phages are predicted to be obligately lytic with little potential for transduction, and no drug-resistance or bacterial virulence genes were identified in their genomes.

TABLE 4

Features of selected *E. coli* phages

| Phage | Size (Kb) | Predicted Morphology | No. Protein-Coding Genes |
|---|---|---|---|
| Ec34 | 167.9 | myovirus | 271 |
| Ec35 | 167.2 | myovirus | 271 |
| Ec45 | 167.5 | myovirus | 267 |
| Ec57 | 167.0 | myovirus | 270 |

TABLE 5

Host Range activity of selected *E. coli* phages

|  | Ec34 | Ec35 | Ec45 | Ec57 |
|---|---|---|---|---|
| *E coli* ID # 2851 | 2.00E+07 | 2.00E+08 | 2.00E+06 | 4.00E+07 |

Confirmation of In Vitro Activity in Broth Culture

Method: 96 well culture plates were prepared with each test well containing 200 μl of a 1/100 overnight culture of *E. coli* PL1 (pks+*E. coli*) AmpliPhi ID #2851 in nutrient broth. Twenty (20) μL of phages Ec34, Ec35, Ec45 and Ec57 and Phage mix D (combination of Ec34, Ec45, and Ec57) were added to the appropriate wells. Control wells containing only bacteria were included. The plates were placed in the Spectrostar plate reader and incubated at 37° C. with shaking. OD readings at 600 nm were taken every 15 minutes for 16 hours.

Growth of the *E. coli* (pks+*E. coli*)—AmpliPhi ID #2851 was partially reduced by the individual phages Ec34, Ec35, and Ec57. Ec45 showed no effect on the growth of the bacteria.

Growth was totally prevented by mix D (Ec34, Ec35, and Ec57). This indicates that the collective bactericidal effect of the 3-phage combination was greater than the simple additive effects of the individual phages.

Example 4. Demonstration of Efficacy in a Mouse Model

Testing of *E. coli*-targeting phages and/or *B. fragilis*-targeting phages in preclinical model (AOM mouse model of colorectal cancer) may be undertaken to demonstrate evidence of efficacy (impact on survival).

Specific pathogen free (SPF) C57BL/6J mice are treated with AOM (Azoxymethane) (10 mg/kg weekly for 6 weeks). AOM induces colorectal cancer in mice and rats. AOM is given weekly until the time of mouse harvest. Prior to inoculation of bacterial strains 6-week-old mice are given water containing 500 mg/L cefoxitin for 48 hours. Cefoxitin treatment results in an absence of detectable bacteria by culture or 16S rRNA qPCR by 24 hours (C. E. DeStefano Shields, S. W. Van Meerbeke, F. Housseau, H. Wang, D. L. Huso, R. A. Casero Jr., H. M. O'Hagan, C. L. Sears, Reduction of murine colon tumorigenesis driven by enterotoxigenic *Bacteroides fragilis* using cefoxitin treatment. J. Infect. Dis. 214, 122-129 (2016)). After removal of antibiotic water for 24 hours, mice are inoculated by oral gavage with $10^8$ colony-forming units (cfu) ETBF or $10^8$ cfu pks+*E. coli* or a mixture containing $10^8$ cfu of each strain. Colonization is confirmed and quantified by collection and cultivation of stool on selective media.

Bacteriophage treatment with the compositions provided herein may be provided in a subset of experimental mice. Analysis of survival of bacteriophage treated and untreated mice may be undertaken.

Example 5. Evaluate Impact of Bacteriophage Treatment on the GI Microbiome

To test whether eliminating pathogenic strains of *E. coli* and/or *B. fragilis* leads to repopulation of the microbiome by benign strains of the same species, microbiome analysis will be undertaken.

Protocols for microbiome analysis have been described (e.g. *Front Cell Infect Microbiol.* 2018; 8: 301). One such protocol includes fecal collection, DNA extraction, and 16S rRNA gene V4 region sequencing. In these experiments, fecal collection is undertaken and the sample is immediately frozen at −20° C. without preservative. Alternatively, reagents such as OMNIgene GUT, 95% ethanol, RNAlater, and Flinders Technology Associates (FTA) cards may be utilized. Samples from a patient include before and after bacteriophage treatment in order to assess the impact of bacteriophage treatment on microbiome profiles.

Standard DNA extraction methods are utilized. One such method includes total DNA extraction from stool samples with the PowerLyzer PowerSoil DNA Isolation Kit (MO BIO laboratories Inc., Carlsbad, CA), following the manufacturer's protocol. The DNA is isolated by column purification and collected in 100 μL of elution buffer (Solution C6).

PCR amplification may be performed, for example of the V4 hypervariable region of the 16S rRNA gene using primers 16SV4_515F and 16SV4_806R (Caporaso J. G., Lauber C. L., Walters W. A., Berg-Lyons D., Huntley J., Fierer N., et al. (2012)). Ultra-high-throughput microbial community analysis on the illumina HiSeq and MiSeq platforms. *ISME J.* 6, 1621-1624) each with 12-bp unique Golay barcodes, resulting in unique dual barcodes for each forward and reverse primer pair. PCR reactions are performed on extracted DNA using appropriate thermal cycling conditions, such as an initial denaturation at 95° C. for 5 min; followed by 15 cycles at 95° C. for 1 min, 55° C. for 1 min, and 68° C. for 1 min; followed by 15 cycles at 95° C. for 1 min, 60° C. for 1 min, and 68° C. for 1 min; and a final extension for 10 min at 68° C.

Dual indexed PCR products are isolated and combined and 100 μL of the pooled products run on a 4% agarose gel at 80 V for 2 h. The bands (~450 bp) may be excised from the agarose gel and purified using a QIAquick Gel Extraction Kit (QIAGEN, Valencia, CA) and eluted in 30 μl of elution buffer.

A sequencing library may be prepared using, for example, the KAPA LTP Library Preparation Kit (Roche Sequencing Solutions, Pleasanton, CA) according to the manufacture's protocol. High-throughput amplicon sequencing is conducted, for example on a MiSeq (Illumina, San Diego, CA) using 2×300 paired-end fragment reads.

Microbiome bioinformatics analysis can be performed using appropriate standard software, such as but not limited to Quantitative Insights Into Microbial Ecology (QIIME) software package, version 1.9 (Caporaso J. G., Kuczynski J., Stombaugh J., Bittinger K., Bushman F. D., Costello E. K., et al. (2010) QIIME allows analysis of high-throughput community sequencing data. *Nat. Methods* 7, 335-336).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

P Embodiments

Embodiment P1. A method of treating or preventing a bacterial-associated cancer in a patient, the method comprising administering to the patient a composition comprising at least two bacteriophages, wherein the cancer is associated with infection by bacteria, and further wherein the bacteriophages target the bacteria.

Embodiment P2. The method of embodiment P1, wherein the bacterial-associated cancer is colorectal cancer, esophageal cancer, gallbladder cancer, lung cancer, squamous cell carcinoma, bladder cancer, stomach cancer, or MALT lymphoma.

Embodiment P3. The method of embodiment P1 or P2, wherein the bacteria comprise *Escherichia coli, Bacteroides fragilis, Helicobacter pylori, Salmonella Typhi, Streptococcus bovis, Chlamydia pneumonia, mycoplasma, Helicobacter hepaticus*, and/or *Schistosoma haematobium*.

Embodiment P4. The method of any one of the above embodiments, wherein the bacteria comprise *E. coli* and/or *B. fragilis*.

Embodiment P5. The method of embodiment P4, wherein the *E. coli* are pks+*E. coli*.

Embodiment P6. The method of embodiment P4 or P5, wherein the *B. fragilis* are enterotoxigenic *Bacteroides fragilis* (ETBF).

Embodiment P7. The method of any one of the preceding embodiments, wherein the bacteriophages are specific for the bacteria and do not target other microorganisms.

Embodiment P8. The method of any one of the preceding embodiments, wherein the composition further comprises an antibiotic (e.g., a chemical antibiotic).

Embodiment P9. The method of any one of the preceding embodiments, wherein the patient has been screened for a genetic mutation that predisposes the patient to cancer.

Embodiment P10. The method of any one of the preceding embodiments, wherein the composition further comprises a pharmaceutically acceptable carrier, diluent, excipient or combinations thereof.

Embodiment P11. The method according to embodiment P10, wherein the pharmaceutically acceptable carrier, diluent, excipient or combinations thereof comprises MgSO4.

Embodiment P12. The method of any one of the preceding embodiments, further comprising administering an antibiotic (e.g., a chemical antibiotic) to the subject.

Embodiment P13. The method of any one of the preceding embodiments, wherein the bacteria are characterized by the presence of a bacterial biofilm.

Embodiment P14. The method of any one of the preceding embodiments, wherein the bacteria are resistant to antibiotics.

Embodiment P15. The method of any one of the preceding embodiments, wherein the composition is administered via an aerosolized formulation of the composition.

Embodiment P16. The method of any one of embodiments P1-P14, wherein the composition is administered intravenously.

Embodiment P17. The method of any one of the preceding embodiments, further comprising administering in combination with an immunotherapeutic agent.

Embodiment P18. The method of embodiment P17, wherein the immunotherapeutic agent comprises an immune checkpoint inhibitor.

Embodiment P19. The method of embodiment P17 or P18, wherein the immunotherapeutic agent comprises anti-PD-1, anti-PD-L1, anti-CTLA-4, anti-CD27, or anti-IDO-1.

Embodiment P20. The method of any one of the preceding embodiments, further comprising administering in combination with a chemotherapeutic agent.

Embodiment P21. The method of embodiment P20, wherein the chemotherapeutic agent is 5-Fluorouracil (5-FU), capecitabine, irinotecan, oxaliplatin, Trifluridine and/or tipiracil.

Embodiment P22. A method for treating or preventing colorectal cancer in a patient in need thereof, the method comprising administering to the patient a composition comprising two or more bacteriophages, wherein the bacteriophages target at least one bacterial species that is associated with colorectal cancer.

Embodiment P23. The method of embodiment P22, wherein the patient has been screened for a genetic mutation that predisposes the patient to cancer.

Embodiment P24. The method of embodiment P23, wherein the genetic mutation is familial adenomatous polyposis.

Embodiment P25. The method of any one of embodiments P22-P24, wherein the bacterial species is *E. coli* and/or *B. fragilis*.

Embodiment P26. The method of embodiment P25, wherein the *E. coli* are PKS+*E. coli*.

Embodiment P27. The method of embodiment P25 or P26, wherein the *B. fragilis* are enterotoxigenic *Bacteroides fragilis* (ETBF).

Embodiment P28. The method of any one of embodiments P22-P27, further comprising administering in combination with an immunotherapeutic agent.

Embodiment P29. The method of embodiment P28, wherein the immunotherapeutic agent comprises an immune checkpoint inhibitor.

Embodiment P30. The method of embodiment P28 or P29, wherein the immunotherapeutic agent comprises anti-PD-1, anti-PD-L1, anti-CTLA-4, anti-CD27, or anti-IDO-1.

Embodiment P31. The method of any one of embodiments P22-P30, further comprising administering in combination with a chemotherapeutic agent.

Embodiment P32. The method of embodiment P31, wherein the chemotherapeutic agent is 5-Fluorouracil (5-FU), capecitabine, irinotecan, oxaliplatin, Trifluridine and/or tipiracil.

Embodiment P33. The method of any one of the above embodiments, wherein the bacteriophages in the composition target one or more oncogenic strains of the bacteria.

Embodiment P34. The method of any one of the above embodiments, wherein the composition minimizes development of bacterial resistance.

Embodiment P35. The method of any one of the above embodiments, wherein the bacteriophages are lytic.

Embodiment P36. A bacteriophage composition comprising one or more bacteriophages that target a carcinogenic bacteria, and a cryoprotectant.

Embodiment P37. The bacteriophage composition of embodiment P36, wherein the cryprotectant comprises glycerol.

SEQUENCE LISTING

The patent contains a lengthy sequence listing. A copy of the sequence listing is available in electronic form from the USPTO web site (https://seqdata.uspto.gov/?pageRequest=docDetail&DocID=US12268720B2). An electronic copy of the sequence listing will also be available from the USPTO upon request and payment of the fee set forth in 37 CFR 1.19(b)(3).

The invention claimed is:

1. A method of treating a bacterial associated cancer bacterial infection in a patient, the method comprising administering to the patient a composition comprising at least two obligately lytic bacteriophages that infect and lyse a bacterium, and wherein a) the bacteriophages are selected from Ec34 (SEQ ID NO:2), Ec35 (SEQ ID NO:3), Ec45 (SEQ ID NO:4), and Ec57 (SEQ ID NO:6), and wherein the target bacteria are *Escherichia coli*; or b) wherein the bacteriophages are selected from Bf1 (deposited with the International Depositary Authority of Canada under Accession No. 040219-02), Bf2 (deposited with the International Depositary Authority of Canada under Accession No. 040219-03), Bf3 (deposited with the International Depositary Authority of Canada under Accession No. 040219-04), and Bf4

(deposited with the International Depositary Authority of Canada under Accession No. 040219-05) and wherein the target bacteria are *Bacteroides fragilis*.

2. The method of claim 1, wherein the patient has a confirmed infection with *Escherichia coli* or *Bacteroides fragilis*.

3. The method of claim 1, wherein the bacterium is associated with a bacterial-associated cancer selected from colorectal cancer, esophageal cancer, gallbladder cancer, lung cancer, squamous cell carcinoma, bladder cancer, stomach cancer, or MALT lymphoma.

4. The method of claim 1, wherein the *E. coli* are pks+*E. coli*, and/or wherein the *Bacteroides fragilis* are enterotoxigenic *Bacteroides fragilis* (ETBF).

5. The method of claim 1, wherein the bacteriophages are specific for the bacteria and do not target other microorganisms.

6. The method of claim 1, wherein the composition further comprises an antibiotic, and/or wherein the method further comprises administering an antibiotic to the subject.

7. The method of claim 1, wherein the patient has been screened for a genetic mutation that predisposes the patient to cancer.

8. The method of claim 1, wherein the composition further comprises a pharmaceutically acceptable carrier, diluent, excipient or combinations thereof comprising calcium salt or magnesium salt.

9. The method of claim 1, wherein the bacteria are characterized by the presence of a bacterial biofilm and are resistant to antibiotics.

10. The method of claim 1, wherein the composition is administered via an oral formulation of the composition.

11. The method of claim 1, wherein the composition is administered intravenously.

12. The method of claim 1, further comprising administering the composition in combination with an immunotherapeutic agent, wherein the immunotherapeutic agent comprises an immune checkpoint inhibitor selected from anti-PD-1, anti-PD-L1, anti-CTLA-4, anti-CD27, or anti-IDO-1.

13. The method of claim 1, further comprising administering the composition in combination with a chemotherapeutic agent, and wherein the chemotherapeutic agent is 5-Fluorouracil (5-FU), capecitabine, irinotecan, oxaliplatin, Trifluridine and/or tipiracil.

14. A method for treating a bacterial infection in a patient in need thereof, the method comprising administering to the patient a composition comprising one or more obligately lytic bacteriophages that infect and lyse a bacterium, wherein the bacteriophages target at least one bacterial species that is associated with colorectal cancer; and wherein
 a) the bacteriophages are selected from Ec34 (SEQ ID NO:2), Ec35 (SEQ ID NO:3), Ec45 (SEQ ID NO:4), and Ec57 (SEQ ID NO:6), and wherein the target bacteria are *Escherichia coli*; or
 b) wherein the bacteriophages are selected from Bf1 (deposited with the International Depositary Authority of Canada under Accession No. 040219-02), Bf2 (deposited with the International Depositary Authority of Canada under Accession No. 040219-03), Bf3 (deposited with the International Depositary Authority of Canada under Accession No. 040219-04), and Bf4 (deposited with the International Depositary Authority of Canada under Accession No. 040219-05) and wherein the target bacteria are *Bacteroides fragilis*.

15. A human therapeutic bacteriophage composition formulated for treating a bacterial infection in a subject in need thereof, comprising one or more obligately lytic bacteriophages that infect and lyse a bacterium, the bacteriophages having a narrow spectrum of activity against the target bacteria, wherein each individual bacteriophage is not prone to generalized transduction and does not carry antibiotic resistance genes, wherein the composition is substantially free of bacterial components; wherein the composition comprises a single dosage of $1 \times 10^5$ to $1 \times 10^{11}$ PFU of each phage per mL of composition; and wherein
 a) the bacteriophages are selected from Ec34 (SEQ ID NO:2), Ec35 (SEQ ID NO:3), Ec45 (SEQ ID NO:4), and Ec57 (SEQ ID NO:6), and wherein the target bacteria are *Escherichia coli*; or
 b) wherein the bacteriophages are selected from Bf1 (deposited with the International Depositary Authority of Canada under Accession No. 040219-02), Bf2 (deposited with the International Depositary Authority of Canada under Accession No. 040219-03), Bf3 (deposited with the International Depositary Authority of Canada under Accession No. 040219-04), and Bf4 (deposited with the International Depositary Authority of Canada under Accession No. 040219-05) and wherein the target bacteria are *Bacteroides fragilis*.

16. The method of claim 1, wherein the composition further comprises a cryoprotectant, and wherein the cryoprotectant comprises 10% sucrose or between about 5% and about 50% glycerol.

17. The method of claim 1, comprising about a 1:1 ratio of the at least two of bacteriophages.

18. A composition comprising a bacteriophage composition according to claim 15, formulated for oral delivery.

19. A composition comprising a bacteriophage composition according to claim 15, wherein the composition is frozen, lyophilized, liquid, or solid.

20. A method of treating a bacterial infection comprising:
 a) selecting a patient with a confirmed bacterial-associated cancer and,
 b) administering the bacteriophage composition according to claim 15 to the subject.

21. A kit comprising:
 a. A bacteriophage composition according to claim 15; and
 b. Instructions for use of same.

22. The method of claim 1, wherein the patient is known to have a cancer.

23. The method of claim 22, wherein the cancer is selected from the group consisting of colorectal cancer, esophageal cancer, gallbladder cancer, lung cancer, squamous cell carcinoma, bladder cancer, stomach cancer, or MALT lymphoma.

24. The method of claim 1, wherein the patient is known to have a colorectal cancer.

* * * * *